United States Patent [19]
Bryant et al.

[11] Patent Number: 5,917,095
[45] Date of Patent: *Jun. 29, 1999

[54] METAL-LIGAND COMPLEX CATALYZED PROCESSES

[75] Inventors: David Robert Bryant, South Charleston; James Clair Nicholson, St. Albans; John Robert Briggs, Charleston; Diane Lee Packett, South Charleston; John Michael Maher, Charleston, all of W. Va.

[73] Assignee: Union Carbide Chemicals & Plastics Technology Corporation, Danbury, Conn.

[ * ] Notice: This patent is subject to a terminal disclaimer.

[21] Appl. No.: 08/814,854

[22] Filed: Mar. 11, 1997

Related U.S. Application Data

[63] Continuation-in-part of application No. 08/756,786, Nov. 26, 1996, Pat. No. 5,789,625, and a continuation-in-part of application No. 08/757,742, Nov. 26, 1996, Pat. No. 5,763,671.

[51] Int. Cl.⁶ ..................................................... C07C 45/50
[52] U.S. Cl. ............................................ 568/454; 568/451
[58] Field of Search ....................................... 568/451, 454

[56] References Cited

U.S. PATENT DOCUMENTS

| | | |
|---|---|---|
| 3,555,098 | 1/1971 | Olivier et al. . |
| 5,288,918 | 2/1994 | Maher et al. ............................ 568/454 |

FOREIGN PATENT DOCUMENTS

| | | |
|---|---|---|
| 0214622 | 3/1987 | European Pat. Off. . |
| 0285136 | 10/1988 | European Pat. Off. . |
| 9616923 | 6/1996 | WIPO . |

*Primary Examiner*—Gary Geist
*Assistant Examiner*—Sreeni Padmanabhan
*Attorney, Agent, or Firm*—Gerald L. Coon

[57] ABSTRACT

This invention relates to a process for separating one or more phosphorus acidic compounds from a reaction product fluid containing said one or more phosphorus acidic compounds, a metal-organophosphorus ligand complex catalyst and optionally free organophosphorus ligand which process comprises (a) treating said reaction product fluid with water sufficient to remove at least some amount of said one or more phosphorus acidic compounds from said reaction product fluid and (b) treating the water which contains phosphorus acidic compounds removed from said reaction product fluid with an acid removal substance sufficient to remove at least some amount of said one or more phosphorus acidic compounds from said water.

20 Claims, 1 Drawing Sheet

METAL-LIGAND COMPLEX CATALYZED PROCESSES

This application is a continuation-in-part of U.S. patent application Ser. Nos. 08/757,742 now U.S. Pat. No. 5,763,671, and 08/756,786, and U.S. Pat. No. 5,789,625 both filed Nov. 26, 1996, and both of which are incorporated herein by reference.

BRIEF SUMMARY OF THE INVENTION

1. Technical Field

This invention relates to improved metal-organophosphorus ligand complex catalyzed processes. More particularly this invention relates to the use of one or more acid removal substances for removing phosphorus acidic compounds formed in metal-organophosphorus ligand complex catalyzed processes and thereby preventing and/or lessening hydrolytic degradation of the organophosphorus ligand and deactivation of the metal-organophosphorus ligand complex catalyst of such processes.

2. Background of the Invention

It is known in the art that various products may be produced by reacting one or more reactants in the presence of an metal-organophosphorus ligand complex catalyst. However, stabilization of the catalyst and organophosphorus ligand remains a primary concern of the art. Obviously catalyst stability is a key issue in the employment of any catalyst. Loss of catalyst or catalytic activity due to undesirable reactions of the highly expensive metal catalysts can be detrimental to the production of the desired product. Likewise degradation of the organophosphorus ligand employed during the process can lead to poisoning organophosphorus compounds or inhibitors or acidic byproducts that can lower the catalytic activity of the metal catalyst. Moreover, production costs of the product obviously increase when productivity of the catalyst decreases.

For instance, a major cause of organophosphite ligand degradation and catalyst deactivation of metal-organophosphite ligand complex catalyzed hydroformylation processes is due to the hydrolytic instability of the organophosphite ligands. All organophosphites are susceptible to hydrolysis in one degree or another, the rate of hydrolysis of organophosphites in general being dependent on the stereochemical nature of the organophosphite. In general, the bulkier the steric environment around the phosphorus atom, the slower the hydrolysis rate. For example, tertiary triorganophosphites such as triphenylphosphite are more susceptible to hydrolysis than diorganophosphites, such as disclosed in U.S. Pat. No. 4,737,588, and organopolyphosphites such as disclosed in U.S. Pat. Nos. 4,748,261 and 4,769,498. Moreover, all such hydrolysis reactions invariably produce phosphorus acidic compounds which catalyze the hydrolysis reactions. For example, the hydrolysis of a tertiary organophosphite produces a phosphonic acid diester, which is hydrolyzable to a phosphonic acid monoester, which in turn is hydrolyzable to $H_3PO_3$ acid. Moreover, hydrolysis of the ancillary products of side reactions, such as between a phosphonic acid diester and the aldehyde or between certain organophosphite ligands and an aldehyde, can lead to production of undesirable strong aldehyde acids, e.g., n-$C_3H_7CH(OH)P(O)(OH)_2$.

Indeed even highly desirable sterically-hindered organobisphosphites which are not very hydrolyzable can react with the aldehyde product to form poisoning organophosphites, e.g., organomonophosphites, which are not only catalytic inhibitors, but far more susceptible to hydrolysis and the formation of such aldehyde acid byproducts, e.g., hydroxy alkyl phosphonic acids, as shown, for example, in U.S. Pat. Nos. 5,288,918 and 5,364,950. Further, the hydrolysis of organophosphite ligands may be considered as being autocatalytic in view of the production of such phosphorus acidic compounds, e.g., $H_3PO_3$, aldehyde acids such as hydroxy alkyl phosphonic acids, $H_3PO_4$ and the like, and if left unchecked the catalyst system of the continuous liquid recycle hydroformylation process will become more and more acidic in time. Thus in time the eventual build-up of an unacceptable amount of such phosphorus acidic materials can cause the total destruction of the organophosphite present, thereby rendering the hydroformylation catalyst totally ineffective (deactivated) and the valuable rhodium metal susceptible to loss, e.g., due to precipitation and/or depositing on the walls of the reactor.

Another problem associated with hydroformylation processes involves metal salt contamination. See, for example, U.S. Pat. No. 4,143,075. Metal salt contaminants, e.g., iron, zinc, calcium salts and the like, in a hydroformylation reaction product fluid promote the self condensation of aldehydes. Such undesired condensation products of aldehydes include aldol condensation products varying in molecular weight ranging from dimer structures to tetramer structures and greater in terms of molecular weight.

Accordingly, a successful method for preventing and/or lessening such hydrolytic degradation of the organophosphorus ligand and deactivation of the catalyst would be highly desirable to the art.

Disclosure of the Invention

It has now been discovered that one or more acid removal substances, e.g., metal oxides, hydroxides, carbonates and/or carboxylates, may be employed to effectively remove such phosphorus acidic compounds and thus prevent and/or lessen hydrolytic degradation of organophosphorus ligands and deactivation of metal-organophosphorus ligand complex catalysts that may occur over the course of time during processes which employ metal-organophosphorus ligand complex catalysts. It has been discovered that one can use the acidity removing capability of certain acid removal substances with minimal transfer of metal salts to the reaction product fluid. It has also been surprisingly discovered that minimum loss of organophosphorus ligand occurs when a reaction product fluid containing a metal-organophosphorus ligand complex catalyst is contacted with the acid removal substances or is contacted with water and the contacted water thereafter treated with the acid removal substances even at elevated temperatures.

This invention relates in part to a process for separating one or more phosphorus acidic compounds from a reaction product fluid containing said one or more phosphorus acidic compounds, a metal-organophosphorus ligand complex catalyst and optionally free ligand which process comprises (a) treating said reaction product fluid with water sufficient to remove at least some amount of said one or more phosphorus acidic compounds from said reaction product fluid and (b) treating the water which contains phosphorus acidic compounds removed from said reaction product fluid with an acid removal substance sufficient to remove at least some amount of said one or more phosphorus acidic compounds from said water.

This invention also relates in part to a process for stabilizing an organophosphorus ligand against hydrolytic degradation and/or a metal-organophosphorus ligand complex catalyst against deactivation which process comprises (a) treating a reaction product fluid containing a metal-organophosphorus ligand complex catalyst and optionally free organophosphorus ligand and which also contains one or more phosphorus acidic compounds, with water sufficient to remove at least some amount of said one or more phosphorus acidic compounds from said reaction product fluid and (b) treating the water which contains phosphorus acidic compounds removed from said reaction product fluid with an acid removal substance sufficient to remove at least some amount of said one or more phosphorus acidic compounds from said water.

This invention further relates in part to a process for preventing and/or lessening hydrolytic degradation of an organophosphorus ligand and/or deactivation of a metal-organophosphorus ligand complex catalyst which process comprises (a) treating a reaction product fluid containing a metal-organophosphorus ligand complex catalyst and optionally free organophosphorus ligand and which also contains one or more phosphorus acidic compounds, with water sufficient to remove at least some amount of said one or more phosphorus acidic compounds from said reaction product fluid and (b) treating the water which contains phosphorus acidic compounds removed from said reaction product fluid with an acid removal substance sufficient to remove at least some amount of said one or more phosphorus acidic compounds from said water.

This invention yet further relates in part to an improved process which comprises reacting one or more reactants in the presence of a metal-organophosphorus ligand complex catalyst and optionally free organophosphorus ligand to produce a reaction product fluid comprising one or more products, the improvement comprising preventing and/or lessening hydrolytic degradation of any said organophosphorus ligand and deactivation of said metal-organophosphorus ligand complex catalyst by treating at least a portion of said reaction product fluid derived from said process and which also contains phosphorus acidic compounds formed during said process with one or more acid removal substances sufficient to remove at least some amount of the phosphorus acidic compounds from said reaction product fluid.

This invention also relates in part to an improved process for producing one or more products which comprises (i) reacting in at least one reaction zone one or more reactants in the presence of a metal-organophosphorus ligand complex catalyst and optionally free organophosphorus ligand to produce a reaction product fluid comprising one or more products and (ii) separating in at least one separation zone or in said at least one reaction zone the one or more products from said reaction product fluid, the improvement comprising preventing and/or lessening hydrolytic degradation of any said organophosphorus ligand and deactivation of said metal-organophosphorus ligand complex catalyst by (a) treating in at least one scrubber zone at least a portion of said reaction product fluid derived from said process and which also contains phosphorus acidic compounds formed during said process with water sufficient to remove at least some amount of the phosphorus acidic compounds from said reaction product fluid and (b) treating in at least one acid removal zone at least a portion of the water which contains phosphorus acidic compounds removed from said reaction product fluid with one or more acid removal substances sufficient to remove at least some amount of the phosphorus acidic compounds from said water.

This invention further relates in part to an improved process for producing one or more products which comprises (i) reacting in at least one reaction zone one or more reactants in the presence of a metal-organophosphorus ligand complex catalyst and optionally free organophosphorus ligand to produce a reaction product fluid comprising one or more products and (ii) separating in at least one separation zone or in said at least one reaction zone the one or more products from said reaction product fluid, the improvement comprising preventing and/or lessening hydrolytic degradation of any said organophosphorus ligand and deactivation of said metal-organophosphorus ligand complex catalyst by (a) treating in at least one acid removal zone at least a portion of said reaction product fluid derived from said process and which also contains phosphorus acidic compounds formed during said process with one or more acid removal substances sufficient to remove at least some amount of the phosphorus acidic compounds from said reaction product fluid, and (b) returning the treated reaction product fluid to said at least one reaction zone or said at least one separation zone.

This invention yet further relates in part to an improved process for producing one or more products which comprises (i) reacting in at least one reaction zone one or more reactants in the presence of a metal-organophosphorus ligand complex catalyst and optionally free organophosphorus ligand to produce a reaction product fluid comprising one or more products and (ii) separating in at least one separation zone or in said at least one reaction zone the one or more products from said reaction product fluid, the improvement comprising preventing and/or lessening hydrolytic degradation of any said organophosphorus ligand and deactivation of said metal-organophosphorus ligand complex catalyst by (a) treating in at least one scrubber zone at least a portion of said reaction product fluid derived from said process and which also contains phosphorus acidic compounds formed during said process with water sufficient to remove at least some amount of the phosphorus acidic compounds from said reaction product fluid, (b) returning the treated reaction product fluid to said at least one reaction zone or said at least one separation zone, (c) treating in at least one acid removal zone at least a portion of the water which contains phosphorus acidic compounds removed from said reaction product fluid with one or more acid removal substances sufficient to remove at least some amount of the phosphorus acidic compounds from said water, and (d) returning the treated water to said at least one scrubber zone.

This invention also relates in part to an improved process for producing one or more products which comprises (i) reacting in at least one reaction zone one or more reactants in the presence of a metal-organophosphorus ligand complex catalyst and optionally free organophosphorus ligand to produce a reaction product fluid comprising one or more products and (ii) separating in at least one separation zone or in said at least one reaction zone the one or more products from said reaction product fluid, the improvement comprising preventing and/or lessening hydrolytic degradation of any said organophosphorus ligand and deactivation of said metal-organophosphorus ligand complex catalyst by (a) withdrawing from said at least one reaction zone or said at least one separation zone at least a portion of a reaction product fluid derived from said process and which also contains phosphorus acidic compounds formed during said process, (b) treating in at least one acid removal zone at least a portion of the withdrawn reaction product fluid derived from said process and which also contains phosphorus acidic compounds formed during said process with one or more acid removal substances sufficient to remove at least some amount of the phosphorus acidic compounds from said reaction product fluid, (c) returning the treated reaction product fluid to said at least one reaction zone or said at least one separation zone, and (d) optionally replacing said one or more acid removal substances.

This invention further relates in part to an improved process for producing one or more products which comprises (i) reacting in at least one reaction zone one or more reactants in the presence of a metal-organophosphorus ligand complex catalyst and optionally free organophosphorus ligand to produce a reaction product fluid comprising one or more products and (ii) separating in at least one separation zone or in said at least one reaction zone the one or more products from said reaction product fluid, the improvement comprising preventing and/or lessening hydrolytic degradation of any said organophosphorus ligand and deactivation of said metal-organophosphorus ligand complex catalyst by (a) withdrawing from said at least one reaction zone or said at least one separation zone at least a portion of a reaction product fluid derived from said process and which also contains phosphorus acidic compounds formed during said process, (b) treating in at least one scrubber zone at least a portion of the withdrawn reaction product fluid derived from said process and which also contains phosphorus acidic compounds formed during said process with water sufficient to remove at least some amount of the phosphorus acidic compounds from said reaction product fluid, (c) returning the treated reaction product fluid to said at least one reaction zone or said at least one separation zone, (d) withdrawing from said at least one scrubber zone at least a portion of said water which contains phosphorus acidic compounds removed from said reaction product fluid, (e) treating in at least one acid removal zone at least a portion of the withdrawn water which contains phosphorus acidic compounds removed from said reaction product fluid with one or more acid removal substances sufficient to remove at least some amount of the phosphorus acidic compounds from said water, (f) returning the treated water to said at least one scrubber zone, and (g) optionally replacing said one or more acid removal substances.

This invention yet further relates in part to an improved process for producing one or more products which comprises (i) reacting in at least one reaction zone one or more reactants in the presence of a metal-organophosphorus ligand complex catalyst and optionally free organophosphorus ligand to produce a reaction product fluid comprising one or more products and (ii) separating in at least one separation zone or in said at least one reaction zone the one or more products from said reaction product fluid, the improvement comprising preventing and/or lessening hydrolytic degradation of any said organophosphorus ligand and deactivation of said metal-organophosphorus ligand complex catalyst by treating at least a portion of said reaction product fluid derived from said process and which also contains phosphorus acidic compounds formed during said process by introducing one or more acid removal substances into said at least one reaction zone and/or said at least one separation zone sufficient to remove at least some amount of the phosphorus acidic compounds from said reaction product fluid.

This invention also relates in part to an improved process for producing one or more products which comprises (i) reacting in at least one reaction zone one or more reactants in the presence of a metal-organophosphorus ligand complex catalyst and optionally free organophosphorus ligand to produce a reaction product fluid comprising one or more products and (ii) separating in at least one separation zone or in said at least one reaction zone the one or more products from said reaction product fluid, the improvement comprising preventing and/or lessening hydrolytic degradation of any said organophosphorus ligand and deactivation of said metal-organophosphorus ligand complex catalyst by (a) treating at least a portion of said reaction product fluid derived from said process and which also contains phosphorus acidic compounds formed during said process by introducing water into said at least one reaction zone and/or said at least one separation zone sufficient to remove at least some amount of the phosphorus acidic compounds from said reaction product fluid and (b) treating in at least one acid removal zone at least a portion of the water which contains phosphorus acidic compounds removed from said reaction product fluid with one or more acid removal substances sufficient to remove at least some amount of the phosphorus acidic compounds from said water.

This invention further relates in part to an improved process for producing one or more products which comprises (i) reacting in at least one reaction zone one or more reactants in the presence of a metal-organophosphorus ligand complex catalyst and optionally free organophosphorus ligand to produce a reaction product fluid comprising one or more products and (ii) separating in at least one separation zone or in said at least one reaction zone the one or more products from said reaction product fluid, the improvement comprising preventing and/or lessening hydrolytic degradation of any said organophosphorus ligand and deactivation of said metal-organophosphorus ligand complex catalyst by (a) withdrawing from said at least one reaction zone or said at least one separation zone at least a portion of a reaction product fluid derived from said process and which also contains phosphorus acidic compounds formed during said process, (b) treating in at least one scrubber zone at least a portion of the withdrawn reaction product fluid derived from said process and which also contains phosphorus acidic compounds formed during said process with water sufficient to remove at least some amount of the phosphorus acidic compounds from said reaction product fluid, (c) returning the treated reaction product fluid to said at least one reaction zone or said at least one separation zone, (d) treating in said at least one scrubber zone at least a portion of the water which contains phosphorus acidic compounds removed from said reaction product fluid with one or more acid removal substances sufficient to remove at least some amount of the phosphorus acidic compounds from said water, and (e) optionally replacing said one or more acid removal substances.

This invention relates in part to a process for separating one or more phosphorus acidic compounds from a hydroformylation reaction product fluid containing said one or more phosphorus acidic compounds, a metal-organophosphorus ligand complex catalyst and optionally free organophosphorus ligand which process comprises (a) treating said hydroformylation reaction product fluid with water sufficient to remove at least some amount of said one or more phosphorus acidic compounds from said hydroformylation reaction product fluid and (b) treating the water which contains phosphorus acidic compounds removed from said hydroformylation reaction product fluid with an acid removal substance sufficient to remove at least some amount of said one or more phosphorus acidic compounds from said water.

This invention also relates in part to a process for stabilizing an organophosphorus ligand against hydrolytic degradation and/or a metal-organophosphorus ligand complex catalyst against deactivation which process comprises (a) treating a hydroformylation reaction product fluid containing a metal-organophosphorus ligand complex catalyst and optionally free organophosphorus ligand and which also contains one or more phosphorus acidic compounds, with water sufficient to remove at least some amount of said one or more phosphorus acidic compounds from said hydroformylation reaction product fluid and (b) treating the water which contains phosphorus acidic compounds removed from said hydroformylation reaction product fluid with an acid removal substance sufficient to remove at least some amount of said one or more phosphorus acidic compounds from said water.

This invention further relates in part to a process for preventing and/or lessening hydrolytic degradation of an organophosphorus ligand and/or deactivation of a metal-organophosphorus ligand complex catalyst which process comprises (a) treating a hydroformylation reaction product fluid containing a metal-organophosphorus ligand complex catalyst and optionally free organophosphorus ligand and which also contains one or more phosphorus acidic compounds, with water sufficient to remove at least some amount of said one or more phosphorus acidic compounds from said hydroformylation reaction product fluid and (b) treating the water which contains phosphorus acidic compounds removed from said hydroformylation reaction product fluid with an acid removal substance sufficient to remove at least some amount of said one or more phosphorus acidic compounds from said water.

This invention yet further relates in part to an improved hydroformylation process which comprises reacting one or more olefinic unsaturated compounds with carbon monoxide and hydrogen in the presence of a metal-organophosphorus ligand complex catalyst and optionally free organophosphorus ligand to produce a reaction product fluid comprising one or more aldehydes, the improvement comprising preventing and/or lessening hydrolytic degradation of any said organophosphorus ligand and deactivation of said metal-organophosphorus ligand complex catalyst by treating at least a portion of said reaction product fluid derived from said hydroformylation process and which also contains phosphorus acidic compounds formed during said hydroformylation process with one or more acid removal substances sufficient to remove at least some amount of the phosphorus acidic compounds from said reaction product fluid.

This invention also relates in part to an improved hydroformylation process for producing one or more aldehydes which comprises (i) reacting in at least one reaction zone one or more olefinic unsaturated compounds with carbon monoxide and hydrogen in the presence of a metal-organophosphorus ligand complex catalyst and optionally free organophosphorus ligand to produce a reaction product fluid comprising one or more aldehydes and (ii) separating in at least one separation zone or in said at least one reaction zone the one or more aldehydes from said reaction product fluid, the improvement comprising preventing and/or lessening hydrolytic degradation of any said organophosphorus ligand and deactivation of said metal-organophosphorus ligand complex catalyst by (a) treating in at least one scrubber zone at least a portion of said reaction product fluid derived from said hydroformylation process and which also contains phosphorus acidic compounds formed during said hydroformylation process with water sufficient to remove at least some amount of the phosphorus acidic compounds from said reaction product fluid and (b) treating in at least one acid removal zone at least a portion of the water which contains phosphorus acidic compounds removed from said reaction product fluid with one or more acid removal substances sufficient to remove at least some amount of the phosphorus acidic compounds from said water.

This invention further relates in part to an improved hydroformylation process for producing one or more aldehydes which comprises (i) reacting in at least one reaction zone one or more olefinic unsaturated compounds with carbon monoxide and hydrogen in the presence of a metal-organophosphorus ligand complex catalyst and optionally free organophosphorus ligand to produce a reaction product fluid comprising one or more aldehydes and (ii) separating in at least one separation zone or in said at least one reaction zone the one or more aldehydes from said reaction product fluid, the improvement comprising preventing and/or lessening hydrolytic degradation of any said organophosphorus ligand and deactivation of said metal-organophosphorus ligand complex catalyst by (a) treating in at least one acid removal zone at least a portion of said reaction product fluid derived from said hydroformylation process and which also contains phosphorus acidic compounds formed during said hydroformylation process with one or more acid removal substances sufficient to remove at least some amount of the phosphorus acidic compounds from said reaction product fluid, and (b) returning the treated reaction product fluid to said at least one separation zone or said at least one reaction zone.

This invention yet further relates in part to an improved hydroformylation process for producing one or more aldehydes which comprises (i) reacting in at least one reaction zone one or more olefinic unsaturated compounds with carbon monoxide and hydrogen in the presence of a metal-organophosphorus ligand complex catalyst and optionally free organophosphorus ligand to produce a reaction product fluid comprising one or more aldehydes and (ii) separating in at least one separation zone or in said at least one reaction zone the one or more aldehydes from said reaction product fluid, the improvement comprising preventing and/or lessening hydrolytic degradation of any said organophosphorus ligand and deactivation of said metal-organophosphorus ligand complex catalyst by (a) treating in at least one scrubber zone at least a portion of said reaction product fluid derived from said hydroformylation process and which also contains phosphorus acidic compounds formed during said hydroformylation process with water sufficient to remove at least some amount of the phosphorus acidic compounds from said reaction product fluid, (b) returning the treated reaction product fluid to said at least one reaction zone or said at least one separation zone, (c) treating in at least one acid removal zone at least a portion of the water which contains phosphorus acidic compounds removed from said reaction product fluid with one or more acid removal substances sufficient to remove at least some amount of the phosphorus acidic compounds from said water, and (d) returning the treated water to said at least one scrubber zone.

This invention also relates in part to an improved hydroformylation process for producing aldehydes which comprises (i) reacting in at least one reaction zone one or more olefinic unsaturated compounds with carbon monoxide and hydrogen in the presence of a metal-organophosphorus ligand complex catalyst and optionally free organophosphorus ligand to produce a reaction product fluid comprising one or more aldehydes and (ii) separating in at least one separation zone or in said at least one reaction zone the one or more aldehydes from said reaction product fluid, the improvement comprising preventing and/or lessening hydrolytic degradation of any said organophosphorus ligand and deactivation of said metal-organophosphorus ligand complex catalyst by (a) withdrawing from said at least one reaction zone or said at least one separation zone at least a portion of said reaction product fluid derived from said hydroformylation process and which also contains phosphorus acidic compounds formed during said hydroformylation process, (b) treating in at least one acid removal zone at least a portion of the withdrawn reaction product fluid derived from said hydroformylation process and which also contains phosphorus acidic compounds formed during said hydroformylation process with one or more acid removal substances sufficient to remove at least some amount of the phosphorus acidic compounds from said reaction product fluid, (c) returning the treated reaction product fluid to said at least one reaction zone or said at least one separation zone, and (d) optionally replacing said one or more acid removal substances.

This invention further relates in part to an improved hydroformylation process for producing aldehydes which comprises (i) reacting in at least one reaction zone one or more olefinic unsaturated compounds with carbon monoxide and hydrogen in the presence of a metal-organophosphorus ligand complex catalyst and optionally free organophosphorus ligand to produce a reaction product fluid comprising one or more aldehydes and (ii) separating in at least one separation zone or in said at least one reaction zone the one or more aldehydes from said reaction product fluid, the improvement comprising preventing and/or lessening hydrolytic degradation of any said organophosphorus ligand and deactivation of said metal-organophosphorus ligand complex catalyst by (a) withdrawing from said at least one reaction zone or said at least one separation zone at least a portion of said reaction product fluid derived from said hydroformylation process and which also contains phosphorus acidic compounds formed during said hydroformylation process, (b) treating in at least one scrubber zone at least a portion of the withdrawn reaction product fluid derived from said hydroformylation process and which also contains phosphorus acidic compounds formed during said hydroformylation process with water sufficient to remove at least some amount of the phosphorus acidic compounds from said reaction product fluid, (c) returning the treated reaction product fluid to said at least one reaction zone or said at least one separation zone, (d) withdrawing from said at least one scrubber zone at least a portion of said water which contains phosphorus acidic compounds removed from said reaction product fluid, (e) treating in at least one acid removal zone at least a portion of the withdrawn water which contains phosphorus acidic compounds removed from said reaction product fluid with one or more acid removal substances sufficient to remove at least some amount of the phosphorus acidic compounds from said water, (f) returning the treated water to said at least one scrubber zone, and (g) optionally replacing said one or more acid removal substances.

This invention yet further relates in part to an improved hydroformylation process for producing one or more aldehydes which comprises (i) reacting in at least one reaction zone one or more olefinic unsaturated compounds with carbon monoxide and hydrogen in the presence of a metal-organophosphorus ligand complex catalyst and optionally free organophosphorus ligand to produce a reaction product fluid comprising one or more aldehydes and (ii) separating in at least one separation zone or in said at least one reaction zone the one or more aldehydes from said reaction product fluid, the improvement comprising preventing and/or lessening hydrolytic degradation of any said organophosphorus ligand and deactivation of said metal-organophosphorus ligand complex catalyst by treating at least a portion of said reaction product fluid derived from said hydroformylation process and which also contains phosphorus acidic compounds formed during said hydroformylation process by introducing one or more acid removal substances into said at least one reaction zone and/or said at least one separation zone sufficient to remove at least some amount of the phosphorus acidic compounds from said reaction product fluid.

This invention also relates in part to an improved hydroformylation process for producing one or more aldehydes which comprises (i) reacting in at least one reaction zone one or more olefinic unsaturated compounds with carbon monoxide and hydrogen in the presence of a metal-organophosphorus ligand complex catalyst and optionally free organophosphorus ligand to produce a reaction product fluid comprising one or more aldehydes and (ii) separating in at least one separation zone or in said at least one reaction zone the one or more aldehydes from said reaction product fluid, the improvement comprising preventing and/or lessening hydrolytic degradation of any said organophosphorus ligand and deactivation of said metal-organophosphorus ligand complex catalyst by (a) treating at least a portion of said reaction product fluid derived from said hydroformylation process and which also contains phosphorus acidic compounds formed during said hydroformylation process by introducing water into said at least one reaction zone and/or said at least one separation zone sufficient to remove at least some amount of the phosphorus acidic compounds from said reaction product fluid and (b) treating in at least one acid removal zone at least a portion of the water which contains phosphorus acidic compounds removed from said reaction product fluid with one or more acid removal substances sufficient to remove at least some amount of the phosphorus acidic compounds from said water.

This invention further relates in part to an improved hydroformylation process for producing aldehydes which comprises (i) reacting in at least one reaction zone one or more olefinic unsaturated compounds with carbon monoxide and hydrogen in the presence of a metal-organophosphorus ligand complex catalyst and optionally free organophosphorus ligand to produce a reaction product fluid comprising one or more aldehydes and (ii) separating in at least one separation zone or in said at least one reaction zone the one or more aldehydes from said reaction product fluid, the improvement comprising preventing and/or lessening hydrolytic degradation of any said organophosphorus ligand and deactivation of said metal-organophosphorus ligand complex catalyst by (a) withdrawing from said at least one reaction zone or said at least one separation zone at least a portion of said reaction product fluid derived from said hydroformylation process and which also contains phosphorus acidic compounds formed during said hydroformylation process, (b) treating in at least one scrubber zone at least a portion of the withdrawn reaction product fluid derived from said hydroformylation process and which also contains phosphorus acidic compounds formed during said hydroformylation process with water sufficient to remove at least some amount of the phosphorus acidic compounds from said reaction product fluid, (c) returning the treated reaction product fluid to said at least one reaction zone or said at least one separation zone, (d) treating in said at least one scrubber zone at least a portion of the water which contains phosphorus acidic compounds removed from said reaction product fluid with one or more acid removal substances sufficient to remove at least some amount of the phosphorus acidic compounds from said water, and (e) optionally replacing said one or more acid removal substances.

Figure 1:
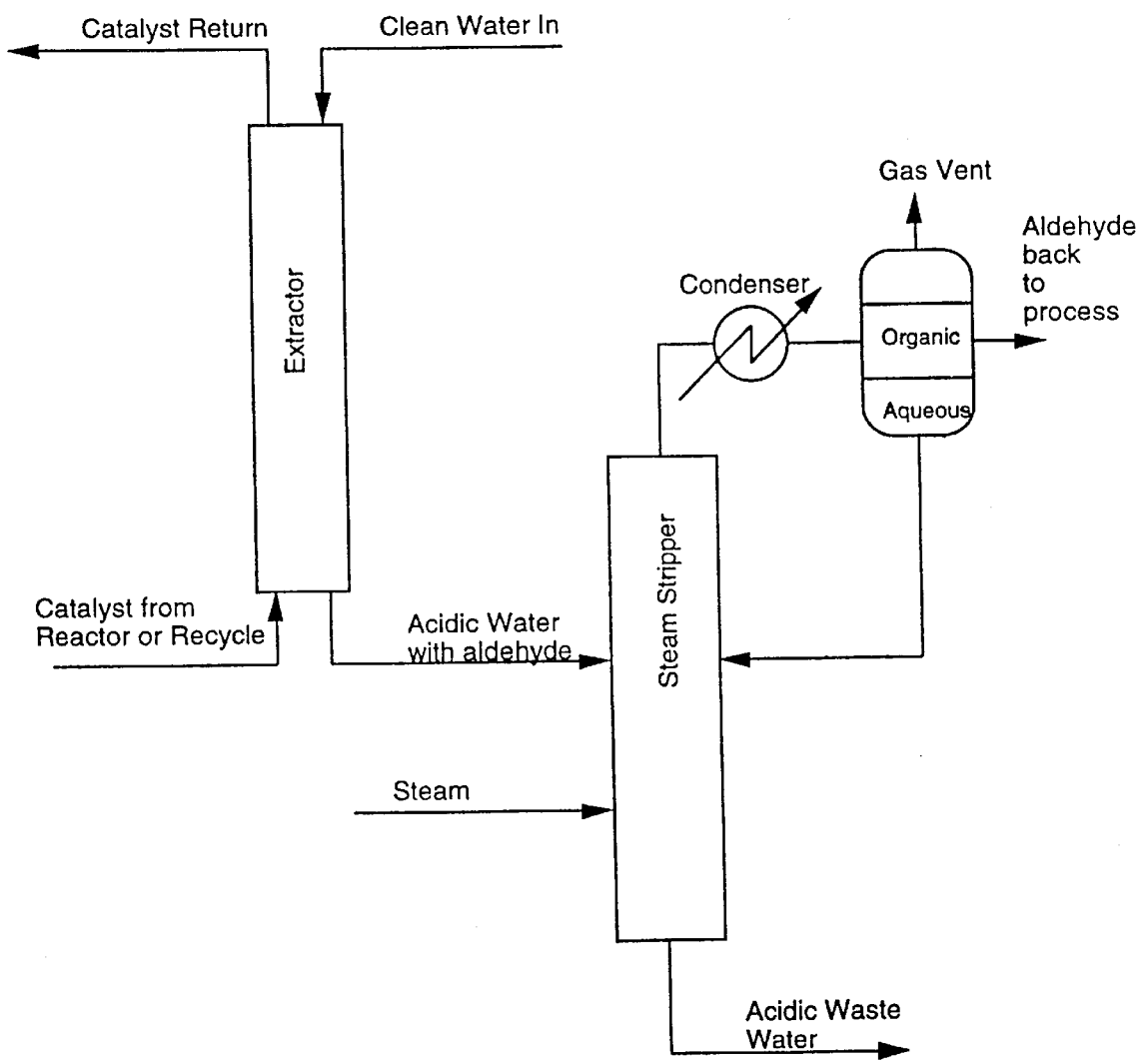
FIG. 1 is a simplified process flow diagram of a process for recovering and returning one or more aldehydes removed by water extraction to the hydroformylation process in accordance with this invention.

DETAILED DESCRIPTION
General Processes

The processes of this invention may be asymmetric or non-asymmetric, the preferred processes being non-asymmetric, and may be conducted in any continuous or semi-continuous fashion and may involve any catalyst liquid and/or gas recycle operation desired. The particular processes for producing products from one or more reactants, as well as the reaction conditions and ingredients of the processes are not critical features of this invention. The processing techniques of this invention may correspond to any of the known processing techniques heretofore employed in conventional processes. For instance, the processes can be conducted in either the liquid or gaseous states and in a continuous, semi-continuous or batch fashion and involve a liquid recycle and/or gas recycle operation or a combination of such systems as desired. Likewise, the manner or order of addition of the reaction ingredients, catalyst and solvent are also not critical and may be accomplished in any conventional fashion. As used herein, the term "reaction product fluid" is contemplated to include, but not limited to, a reaction mixture containing an amount of any one or more of the following: (a) a metal-organophosphorus ligand complex catalyst, (b) free organophosphorus ligand, (c) one or more phosphorus acidic compounds formed in the reaction, (d) product formed in the reaction, (e) unreacted reactants, and (f) an organic solubilizing agent for said metal-organophosphorus ligand complex catalyst and said free organophosphorus ligand. The reaction product fluid encompasses, but is not limited to, (a) the reaction medium in the reaction zone, (b) the reaction medium stream on its way to the separation zone, (c) the reaction medium in the separation zone, (d) the recycle stream between the separation zone and the reaction zone, (e) the reaction medium withdrawn from the reaction zone or separation zone for treatment with the water, (f) the withdrawn reaction medium treated with the water, (g) the treated reaction medium returned to the reaction zone or separation zone, and (h) reaction medium in external cooler.

This invention encompasses the carrying out of known conventional syntheses in a conventional fashion employing a metal-organophosphorus ligand complex catalyst in which the metal-organophosphorus ligand complex catalyst containing reaction product fluid derived from said process and which also contains phosphorus acidic compounds formed during said process is (a) treated with water sufficient to neutralize and remove at least some amount of said one or more phosphorus acidic compounds from said reaction product fluid and (b) the water which contains phosphorus acidic compounds removed from said reaction product fluid is treated with an acid removal substance sufficient to remove at least some amount of said one or more phosphorus acidic compounds from said water treated with water to prevent and/or lessen hydrolytic degradation of the organophosphorus ligand and deactivation of the metal-organophosphorus ligand complex catalyst.

Illustrative processes include, for example, hydroformylation, hydroacylation (intramolecular and intermolecular), hydrocyanation, hydroamidation, hydroesterification, aminolysis, alcoholysis, carbonylation, olefin isomerization, transfer hydrogenation and the like. Preferred processes involve the reaction of organic compounds with carbon monoxide, or with carbon monoxide and a third reactant, e.g., hydrogen, or with hydrogen cyanide, in the presence of a catalytic amount of a metal-organophosphorus ligand complex catalyst. The most preferred processes include hydroformylation, hydrocyanation and carbonylation.

Hydroformylation can be carried out in accordance with conventional procedures known in the art. For example, aldehydes can be prepared by reacting an olefinic compound, carbon monoxide and hydrogen under hydroformylation conditions in the presence of a metal-organophosphorus ligand complex catalyst described herein. Alternatively, hydroxyaldehydes can be prepared by reacting an epoxide, carbon monoxide and hydrogen under hydroformylation conditions in the presence of a metal-organophosphorus ligand complex catalyst described herein. The hydroxyaldehyde can be hydrogenated to a diol, e.g., hydroxypropionaldehyde can be hydrogenated to propanediol. Hydroformylation processes are described more fully hereinbelow.

Intramolecular hydroacylation can be carried out in accordance with conventional procedures known in the art. For example, aldehydes containing an olefinic group 3 to 7 carbons removed can be converted to cyclic ketones under hydroacylation conditions in the presence of a metal-organophosphorus ligand complex catalyst described herein.

Intermolecular hydroacylation can be carried out in accordance with conventional procedures known in the art. For example, ketones can be prepared by reacting an olefin and an aldehyde under hydroacylation conditions in the presence of a metal-organophosphorus ligand complex catalyst described herein.

Hydrocyanation can be carried out in accordance with conventional procedures known in the art. For example, nitrile compounds can be prepared by reacting an olefinic compound and hydrogen cyanide under hydrocyanation conditions in the presence of a metal-organophosphorus ligand complex catalyst described herein. A preferred hydrocyanation process involves reacting a nonconjugated acyclic aliphatic monoolefin, a monoolefin conjugated to an ester group, e.g., methyl pent-2-eneoate, or a monoolefin nonconjugated to a nitrile group, e.g., 3-pentenenitrile, with a source of hydrogen cyanide in the presence of a catalyst precursor composition comprising zero-valent nickel and a bidentate phosphite ligand to produce a terminal organonitrile, e.g., adiponitrile, alkyl 5-cyanovalerate or 3-(perfluoroalkyl)propionitrile. Preferably, the reaction is carried out in the presence of a Lewis acid promoter. Illustrative hydrocyanation processes are disclosed in U.S. Pat. No. 5,523,453 and WO 95/14659, the disclosures of which are incorporated herein by reference.

Hydroamidation can be carried out in accordance with conventional procedures known in the art. For example, amides can be prepared by reacting an olefin, carbon monoxide and a primary or secondary amine or ammonia under hydroamidation conditions in the presence of a metal-organophosphorus ligand complex catalyst described herein.

Hydroesterification can be carried out in accordance with conventional procedures known in the art. For example, esters can be prepared by reacting an olefin, carbon monoxide and an alcohol under hydroesterification conditions in the presence of a metal-organophosphorus ligand complex catalyst described herein.

Aminolysis can be carried out in accordance with conventional procedures known in the art. For example, amines can be prepared by reacting an olefin with a primary or secondary amine under aminolysis conditions in the presence of a metal-organophosphorus ligand complex catalyst described herein.

Alcoholysis can be carried out in accordance with conventional procedures known in the art. For example, ethers can be prepared by reacting an olefin with an alcohol under alcoholysis conditions in the presence of a metal-organophosphorus ligand complex catalyst described herein.

Carbonylation can be carried out in accordance with conventional procedures known in the art. For example, lactones can be prepared by treatment of allylic alcohols with carbon monoxide under carbonylation conditions in the presence of a metal-organophosphorus ligand complex catalyst described herein.

Isomerization can be carried out in accordance with conventional procedures known in the art. For example, allylic alcohols can be isomerized under isomerization conditions to produce aldehydes in the presence of a metal-organophosphorus ligand complex catalyst described herein.

Transfer hydrogenation can be carried out in accordance with conventional procedures known in the art. For example, alcohols can be prepared by reacting a ketone and an alcohol under transfer hydrogenation conditions in the presence of a metal-organophosphorus ligand complex catalyst described herein.

The permissible starting material reactants encompassed by the processes of this invention are, of course, chosen depending on the particular process desired. Such starting materials are well known in the art and can be used in conventional amounts in accordance with conventional methods. Illustrative starting material reactants include, for example, substituted and unsubstituted aldehydes (intramolecular hydroacylation), olefins (hydroformylation, carbonylation, intermolecular hydroacylation, hydrocyanation, hydroamidation, hydroesterification, aminolysis, alcoholysis), ketones (transfer hydrogenation), epoxides (hydroformylation, hydrocyanation), alcohols (carbonylation) and the like. Illustrative of suitable reactants for effecting the processes of this invention are set out in Kirk-Othmer, Encyclopedia of Chemical Technology, Fourth Edition, 1996, the pertinent portions of which are incorporated herein by reference.

Illustrative metal-organophosphorus ligand complex catalysts employable in the processes encompassed by this invention as well as methods for their preparation are well known in the art and include those disclosed in the below mentioned patents. In general such catalysts may be preformed or formed in situ as described in such references and consist essentially of metal in complex combination with an organophosphorus ligand. The active species may also contain carbon monoxide and/or hydrogen directly bonded to the metal.

The catalyst useful in the processes includes a metal-organophosphorus ligand complex catalyst which can be optically active or non-optically active. The permissible metals which make up the metal-organophosphorus ligand complexes include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium, nickel, palladium and ruthenium, more preferably rhodium, nickel and palladium, especially rhodium. Other permissible metals include Group 11 metals selected from copper (Cu), silver (Ag), gold (Au) and mixtures thereof, and also Group 6 metals selected from chromium (Cr), molybdenum (Mo), tungsten (W) and mixtures thereof. Mixtures of metals from Groups 6, 8, 9, 10 and 11 may also be used in this invention. The permissible organophosphorus ligands which make up the metal-organophosphorus ligand complexes and free organophosphorus ligand include mono-, di-, tri- and higher polyorganophosphorus compounds. Illustrative permissible organophosphorus ligands include, for example, organophosphonites, organophosphinites, organophosphorus oxygen-containing ligands, organophosphorus nitrogen-containing ligands, organophosphorus sulfur-containing ligands and the like. Mixtures of such ligands may be employed if desired in the metal-organophosphorus ligand complex catalyst and/or free ligand and such mixtures may be the same or different. This invention is not intended to be limited in any manner by the permissible organophosphorus ligands or mixtures thereof. It is to be noted that the successful practice of this invention does not depend and is not predicated on the exact structure of the metal-organophosphorus ligand complex species, which may be present in their mononuclear, dinuclear and/or higher nuclearity forms. Indeed, the exact structure is not known. Although it is not intended herein to be bound to any theory or mechanistic discourse, it appears that the catalytic species may in its simplest form consist essentially of the metal in complex combination with the organophosphorus ligand and carbon monoxide and/or hydrogen when used.

The term "complex" as used herein and in the claims means a coordination compound formed by the union of one or more electronically rich molecules or atoms capable of independent existence with one or more electronically poor molecules or atoms, each of which is also capable of independent existence. For example, the organophosphorus ligands employable herein may possess one or more phosphorus donor atoms, each having one available or unshared pair of electrons which are each capable of forming a coordinate covalent bond independently or possibly in concert (e.g., via chelation) with the metal. Carbon monoxide (which is also properly classified as a ligand) can also be present and complexed with the metal. The ultimate composition of the complex catalyst may also contain an additional ligand, e.g., hydrogen or an anion satisfying the coordination sites or nuclear charge of the metal. Illustrative additional ligands include, for example, halogen (Cl, Br, I), alkyl, aryl, substituted aryl, acyl, $CF_3$, $C_2F_5$, CN, $(R)_2PO$ and $RP(O)(OH)O$ (wherein each R is the same or different and is a substituted or unsubstituted hydrocarbon radical, e.g., the alkyl or aryl), acetate, acetylacetonate, $SO_4$, $PF_4$, $PF_6$, $NO_2$, $NO_3$, $CH_3O$, $CH_2$=$CHCH_2$, $CH_3CH$=$CHCH_2$, $C_6H_5CN$, $CH_3CN$, $NH_3$, pyridine, $(C_2H_5)_3N$, mono-olefins, diolefins and triolefins, tetrahydrofaran, and the like. It is of course to be understood that the complex species are preferably free of any additional organic ligand or anion that might poison the catalyst or have an undue adverse effect on catalyst performance. It is preferred in the metal-organophosphorus ligand complex catalyzed processes, e.g., hydroformylation, that the active catalysts be free of halogen and sulfur directly bonded to the metal, although such may not be absolutely necessary.

The number of available coordination sites on such metals is well known in the art. Thus the catalytic species may comprise a complex catalyst mixture, in their monomeric, dimeric or higher nuclearity forms, which are preferably characterized by at least one organophosphorus-containing molecule complexed per one molecule of metal, e.g., rhodium. For instance, it is considered that the catalytic species of the preferred catalyst employed in a hydroformylation reaction may be complexed with carbon monoxide and hydrogen in addition to the organophosphorus ligands in view of the carbon monoxide and hydrogen gas employed by the hydroformylation reaction.

The organophosphorus compounds that may serve as the ligand of the metal-organophosphorus ligand complex catalyst and/or free ligand of the processes and reaction product fluids of this invention may be of the achiral (optically inactive) or chiral (optically active) type and are known in the art. By "free ligand" is meant ligand that is not complexed with (tied to or bound to) the metal, e.g., metal atom, of the complex catalyst. As noted herein, the processes of this invention and especially the hydroformylation process may be carried out in the presence of free organophosphorus ligand. Achiral organophosphorus compounds are preferred.

Among the organophosphorus compounds that may serve as the ligand of the metal-organophosphorus ligand complex catalyst containing reaction product fluids of this invention and/or any free organophosphorus ligand that might also be present in said reaction product fluids are monoorganophosphorus, diorganophosphorus, triorganophosphorus and organopolyphosphorus compounds. For purposes of this invention, such organophosphorus compounds are susceptible to undergoing hydrolytic degradation to produce phosphorus acidic compounds. The organophosphorus ligands employable in this invention may be prepared by methods known in the art. See, for example, WO Patent Application No. 96/16923, published Jun. 6, 1996, the disclosure of which is incorporated herein by reference.

Representative monoorganophosphorus compounds may include those having the formula:

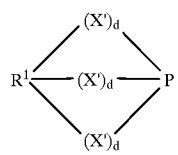

(I)

wherein $R^1$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from diethylenetriamine and the like, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, such as alkylene or arylene, provided at least one X' is other than a substituted or unsubstituted divalent hydrocarbon radical containing from 2 to 40 carbon atoms or greater and at least one X' is other than an oxygen (O) atom, and each d is the same or different and is a value of 0 or 1, provided that the normal valencies of $R^1$, X' and phosphorus (P) are satisfied. It is understood that two or more X' may be combined to form a polycyclic compound. Preferably, at least one X' is an oxygen (O) atom.

Representative diorganophosphorus compounds may include those having the formula:

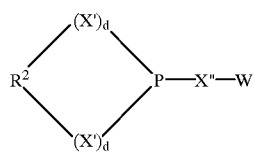

(II)

wherein $R^2$ represents a substituted or unsubstituted divalent hydrocarbon radical containing from 4 to 40 carbon atoms or greater, W represents a substituted or unsubstituted monovalent hydrocarbon radical containing from 1 to 18 carbon atoms or greater, X" represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, such as alkylene or arylene, provided at least one X' and X" is other than a substituted or unsubstituted divalent hydrocarbon radical containing from 2 to 40 carbon atoms or greater and at least one X' and X" is other than an oxygen (O) atom, each d is the same or different and is a value of 0 or 1, provided that the normal valencies of $R^2$, X' and phosphorus (P) are satisfied, and X' is as defined in Formula (I).

Representative substituted and unsubstituted monovalent hydrocarbon radicals represented by W in the above Formula (II) include alkyl and aryl radicals, while representative substituted and unsubstituted divalent hydrocarbon radicals represented by $R^2$ include divalent acyclic radicals and divalent aromatic radicals. Illustrative divalent acyclic radicals include, for example, alkylene, alkylene-oxyalkylene, alkylene-$NR^4$-alkylene wherein $R^4$ is hydrogen or a substituted or unsubstituted monovalent hydrocarbon radical, e.g., an alkyl radical having 1 to 4 carbon atoms; alkylene-S-alkylene, and cycloalkylene radicals, and the like. The more preferred divalent acyclic radicals are the divalent alkylene radicals such as disclosed more fully, for example, in U.S. Pat. Nos. 3,415,906 and 4,567,302 and the like, the disclosures of which are incorporated herein by reference. Illustrative divalent aromatic radicals include, for example, arylene, bisarylene, arylene-alkylene, arylene-alkylene-arylene, arylene-oxy-arylene, arylene-$NR^4$-arylene wherein $R^4$ is as defined above, arylene-S-arylene, and arylene-S-alkylene, and the like. More preferably $R^2$ is a divalent aromatic radical such as disclosed more fully, for example, in U.S. Pat. Nos. 4,599,206, 4,717,775, 4,835,299, and the like, the disclosures of which are incorporated herein by reference.

Representative of a more preferred class of diorganophosphorus compounds are those of the formula:

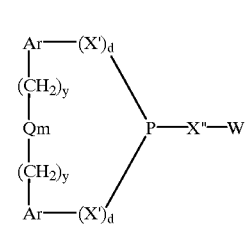

(III)

wherein W, X' and X" are as defined above, each Ar is the same or different and represents a substituted or unsubstituted aryl radical, each y is the same or different and is a value of 0 or 1, Q represents a divalent bridging group selected from —$C(R^3)_2$—, —O—, —S—, —$NR^4$—, $Si(R^5)_2$— and —CO—, wherein each $R^3$ is the same or different and represents hydrogen, an alkyl radical having from 1 to 12 carbon atoms, phenyl, tolyl, and anisyl, $R^4$ is as defined above, each $R^5$ is the same or different and represents hydrogen or a methyl radical, m is a value of 0 or 1, and each d is the same or different and is a value of 0 or 1, provided that the normal valencies of Ar, X' and phosphorus (P) are satisfied.

Representative triorganophosphorus compounds may include those having the formula:

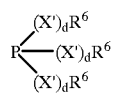
(IV)

wherein each $R^6$ is the same or different and is a substituted or unsubstituted monovalent hydrocarbon radical e.g., an alkyl, cycloalkyl, aryl, alkaryl and aralkyl radicals which may contain from 1 to 24 carbon atoms, each d is the same or different and is a value of 0 or 1, provided that the normal valencies of $R^6$, X' and phosphorus (P) are satisfied, and X' is as defined above.

Representative organopolyphosphorus compounds contain two or more tertiary (trivalent) phosphorus atoms and may include those having the formula:

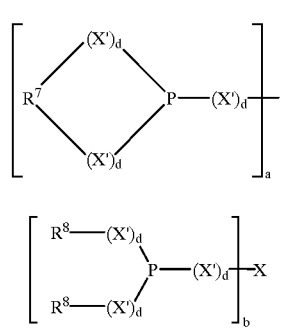
(V)

wherein X represents a substituted or unsubstituted n-valent hydrocarbon bridging radical containing from 2 to 40 carbon atoms, each $R^7$ is the same or different and represents a divalent hydrocarbon radical containing from 4 to 40 carbon atoms, each $R^8$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b, each d is the same or different and is a value of 0 or 1, provided that the normal valencies of $R^7$, $R^8$, X, X' and phosphorus (P) are satisfied, and X' is as defined above. Of course it is to be understood that when a has a value of 2 or more, each $R^7$ radical may be the same or different. Each $R^8$ radical may also be the same or different any given compound. It is also understood that any permissible two or more X' may be combined to form a cyclic radical. Preferably, at least one X' is an oxygen (O) atom.

Representative n-valent (preferably divalent) hydrocarbon bridging radicals represented by X and representative divalent hydrocarbon radicals represented by $R^7$ above, include both acyclic radicals and aromatic radicals, such as alkylene, alkylene-$Q_m$-alkylene, cycloalkylene, arylene, bisarylene, arylene-alkylene, and arylene—$(CH_2)_y$—$Q_m$—$(CH_2)_y$-arylene radicals, and the like, wherein each Q, y and m are as defined above in Formula (III). The more preferred acyclic radicals represented by X and $R^7$ above are divalent alkylene radicals, while the more preferred aromatic radicals represented by X and $R^7$ above are divalent arylene and bisarylene radicals, such as disclosed more fully, for example, in U.S. Pat. Nos. 4,769,498; 4,774,361: 4,885,401; 5,179,055; 5,113,022; 5,202,297; 5,235,113; 5,264,616 and 5,364,950, and European Patent Application Publication No. 662,468, and the like, the disclosures of which are incorporated herein by reference. Representative preferred monovalent hydrocarbon radicals represented by each $R^8$ radical above include alkyl and aromatic radicals.

Illustrative preferred organopolyphosphorus compounds may include bisphosphorus compounds such as those of Formulas (VI) to (VIII) below:

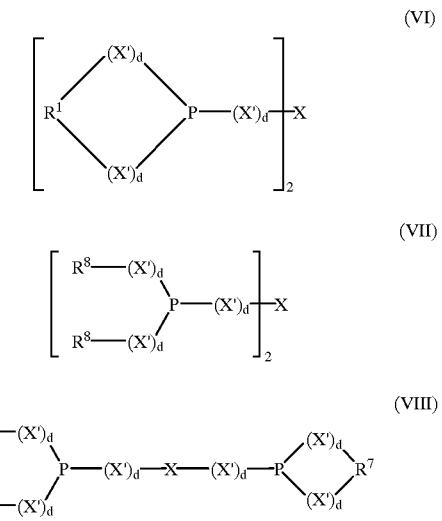

wherein each $R^7$, $R^8$, X, X' and d of Formulas (VI) to (VIII) are the same as defined above for Formula (V). Preferably each $R^7$ and X represents a divalent hydrocarbon radical selected from alkylene, arylene, arylene-alkylene-arylene, and bisarylene, while each $R^8$ radical represents a monovalent hydrocarbon radical selected from alkyl and aryl radicals.

Representative of more preferred classes of organobisphosphorus compounds are those of the following Formulas (IX) to (XI)

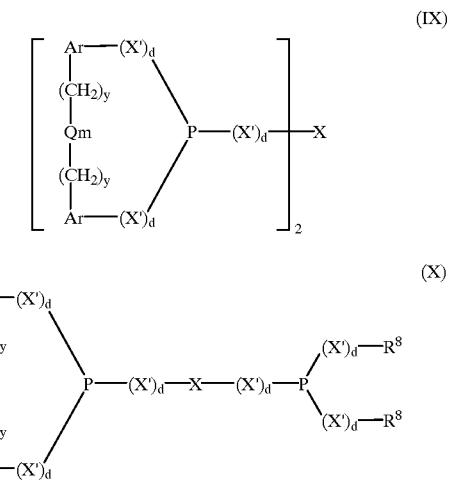

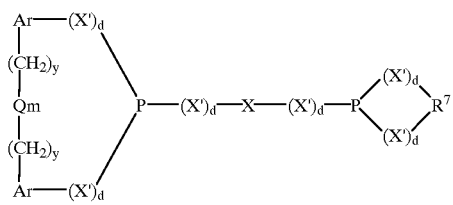

(XI)

wherein Ar, Q, $R^7$, $R^8$, X, X', d, m, and y are as defined above. Most preferably X represents a divalent aryl —$(CH_2)_y$—$(Q)_m$—$(CH_2)_y$—aryl radical wherein each y individually has a value of 0 or 1; m has a value of 0 or 1 and Q is —O—, —S— or —$C(R^3)_2$ where each $R^3$ is the same or different and represents hydrogen or a methyl radical. More preferably each alkyl radical of the above defined $R^8$ groups may contain from 1 to 24 carbon atoms and each aryl radical of the above-defined Ar, X, $R^7$ and $R^8$ groups of the above Formulas (IX) to (XI) may contain from 6 to 18 carbon atoms and said radicals may be the same or different, while the preferred alkylene radicals of X may contain from 2 to 18 carbon atoms and the preferred alkylene radicals of $R^7$ may contain from 5 to 14 carbon atoms. In addition, preferably the divalent Ar radicals and divalent aryl radicals of X of the above formulas are phenylene radicals in which the bridging group represented by —$(CH_2)_y$—$(Q)_m$—$(CH_2)_y$— is bonded to said phenylene radicals in positions that are ortho to the oxygen atoms of the formulas that connect the phenylene radicals to their phosphorus atom of the formulae. It is also preferred that any substituent radical when present on such phenylene radicals be bonded in the para and/or ortho position of the phenylene radicals in relation to the oxygen atom that bonds the given substituted phenylene radical to its phosphorus atom.

Of course any of the $R^1$, $R^2$, $R^6$, $R^7$, $R^8$, W, X, Q and Ar radicals of such organophosphorus compounds of Formulas (I) to (XI) above may be substituted if desired, with any suitable substituent containing from 1 to 30 carbon atoms that does not unduly adversely affect the desired result of the process of this invention. Substituents that may be on said radicals in addition of course to corresponding hydrocarbon radicals such as alkyl, aryl, aralkyl, alkaryl and cyclohexyl substituents, may include for example silyl radicals such as —$Si(R^{10})_3$; amino radicals such as —$N(R^{10})_2$; phosphine radicals such as -aryl—$P(R^{10})_2$; acyl radicals such as —$C(O)R^{10}$ acyloxy radicals such as —$OC(O)R^{10}$; amino radicals such as —$CON(R^{10})_2$ and —$N(R^{10})COR^{10}$; sulfonyl radicals such as —$SO_2R^{10}$, alkoxy radicals such as —$OR^{10}$; sulfinyl radicals such as —$SOR^{10}$, sulfenyl radicals such as —$SR^{10}$, phosphonyl radicals such as —$P(O)(R^{10})_2$, as well as halogen, nitro, cyano, trifluoromethyl, hydroxy radicals, and the like, wherein each $R^{10}$ radical individually represents the same or different monovalent hydrocarbon radical having from 1 to 18 carbon atoms (e.g., alkyl, aryl, aralkyl, alkaryl and cyclohexyl radicals), with the proviso that in amino substituents such as —$N(R^{10})_2$ each $R^{10}$ taken together can also represent a divalent bridging group that forms a heterocyclic radical with the nitrogen atom, and in amido substituents such as —$C(O)N(R^{10})_2$ and —$N(R^{10})COR^{10}$ each $R^{10}$ bonded to N can also be hydrogen. Of course it is to be understood that any of the substituted or unsubstituted hydrocarbon radicals groups that make up a particular given organophosphorus compound may be the same or different.

More specifically illustrative substituents include primary, secondary and tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, decyl, octadecyl, and the like; aryl radicals such as phenyl, naphthyl and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy, —$OCH_2CH_2OCH_3$, —$O(CH_2CH_2)_2OCH_3$, —$O(CH_2CH_2)_3OCH_3$, and the like; aryloxy radicals such as phenoxy and the like; as well as silyl radicals such as —$Si(CH_3)_3$, —$Si(OCH_3)_3$, —$Si(C_3H_7)_3$, and the like; amino radicals such as —$NH_2$, —$N(CH_3)_2$, —$NHCH_3$, —$NH(C_2H_5)$, and the like; arylphosphine radicals such as —$P(C_6H_5)_2$, and the like; acyl radicals such as —$C(O)CH_3$, —$C(O)C_2H_5$, —$C(O)C_6H_5$, and the like; carbonyloxy radicals such as —$C(O)OCH_3$ and the like; oxycarbonyl radicals such as —$O(CO)C_6H_5$, and the like; amido radicals such as —$CONH_2$, —$CON(CH_3)_2$, —$NHC(O)CH_3$, and the like; sulfonyl radicals such as —$S(O)_2$ $C_2H_5$ and the like; sulfinyl radicals such as —$S(O)CH_3$ and the like; sulfenyl radicals such as —$SCH_3$, —$SC_2H_5$, —$SC_6H_5$, and the like; phosphonyl radicals such as —$P(O)(C_6H_5)_2$, —$P(O)(CH_3)_2$, —$P(O)(C_2H_5)_2$, —$P(O)(C_3H_7)_2$, —$P(O)(C_4H_9)_2$, —$P(O)(C_6H_{13})_2$, —$P(O)CH_3(C_6H_5)$, —$P(O)(H)(C_6H_5)$, and the like.

Specific illustrative examples of such organophosphorus ligands include the following:

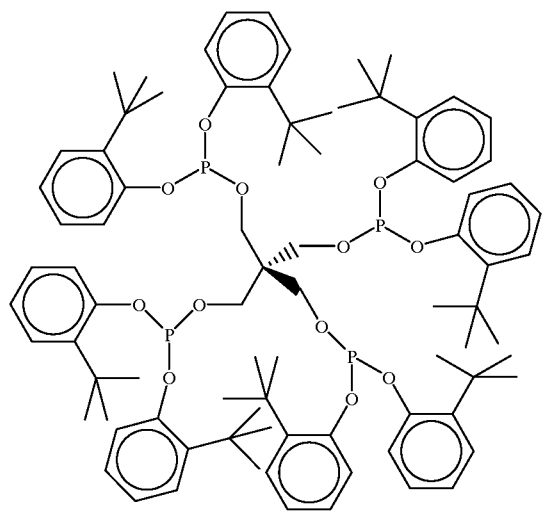
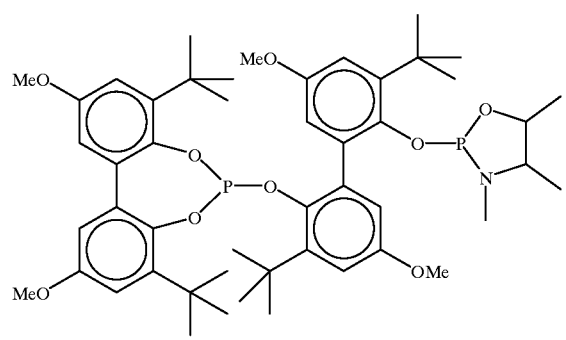
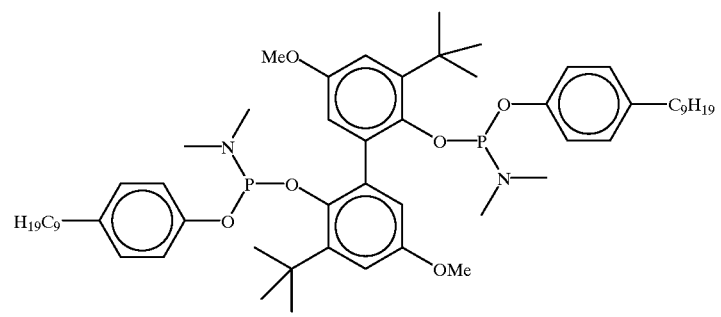
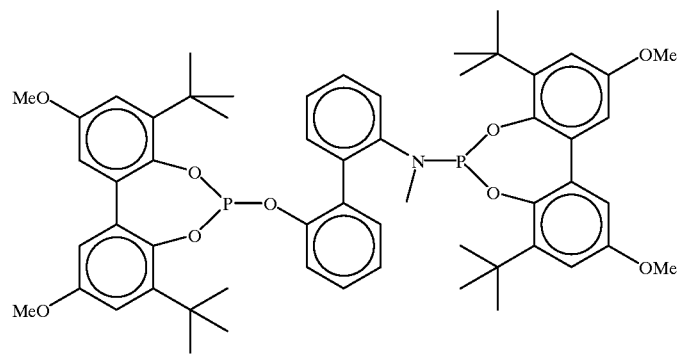

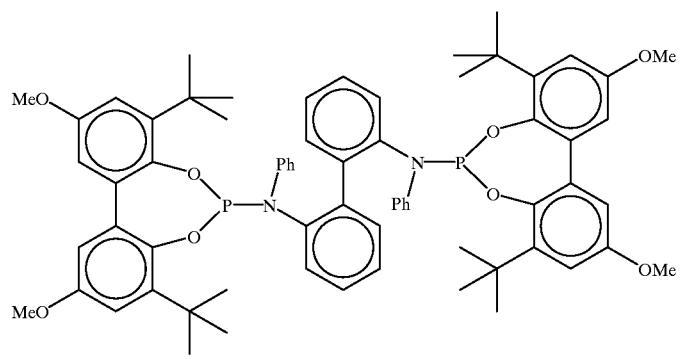
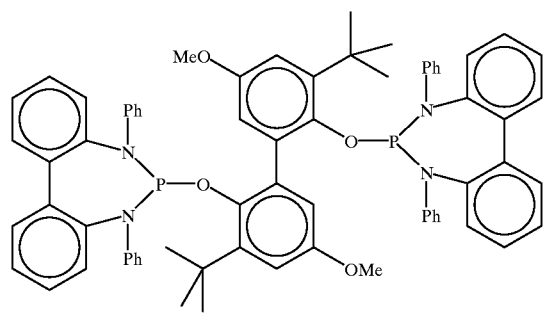
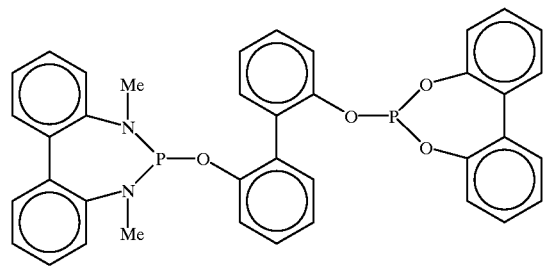
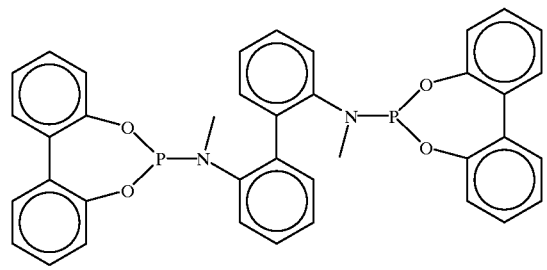
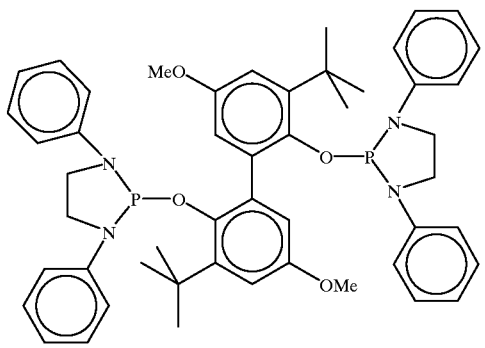

-continued
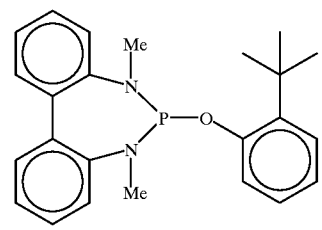
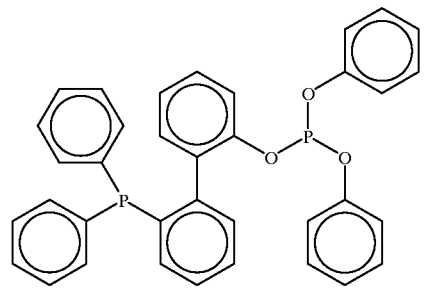
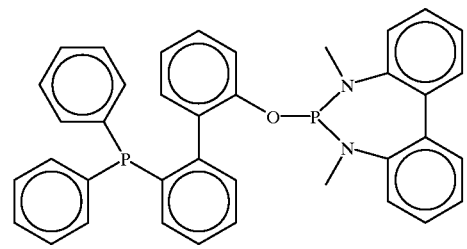
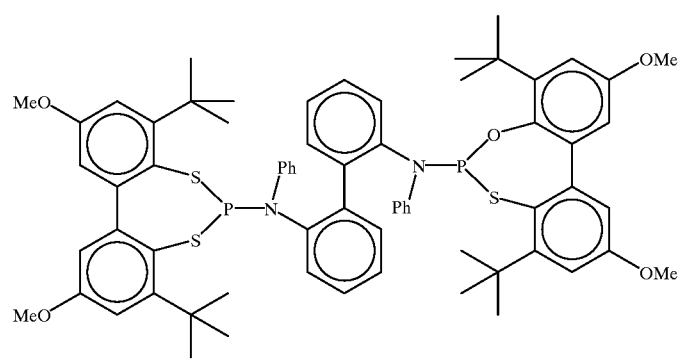
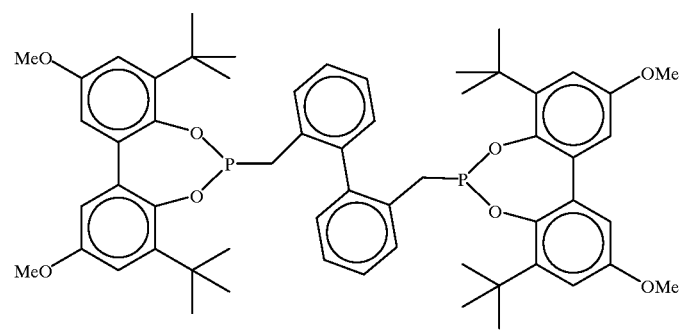

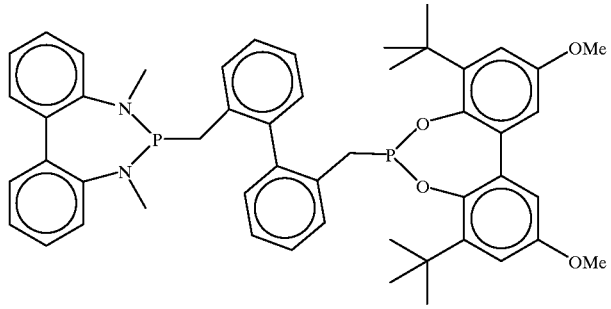

As noted above, the metal-organophosphorus ligand complex catalysts employable in this invention may be formed by methods known in the art. The metal-organophosphorus ligand complex catalysts may be in homogeneous or heterogeneous form. For instance, preformed rhodium hydrido-carbonyl-organophosphorus ligand catalysts may be prepared and introduced into the reaction mixture of a particular process. More preferably, the metal-organophosphorus ligand complex catalysts can be derived from a rhodium catalyst precursor which may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction mixture along with the organophosphorus ligand for the in situ formation of the active catalyst. In a preferred embodiment of this invention, rhodium dicarbonyl acetylacetonate is employed as a rhodium precursor and reacted in the presence of a solvent with the organophosphorus ligand to form a catalytic rhodium-organophosphorus ligand complex precursor which is introduced into the reaction zone along with excess (free) organophosphorus ligand for the in situ formation of the active catalyst. In any event, it is sufficient for the purpose of this invention that carbon monoxide, hydrogen and organophosphorus compound are all ligands that are capable of being complexed with the metal and that an active metal-organophosphorus ligand catalyst is present in the reaction mixture under the conditions used in the hydroformylation reaction.

More particularly, a catalyst precursor composition can be formed consisting essentially of a solubilized metal-organophosphorus ligand complex precursor catalyst, an organic solvent and free organophosphorus ligand. Such precursor compositions may be prepared by forming a solution of a rhodium starting material, such as a rhodium oxide, hydride, carbonyl or salt, e.g., a nitrate, which may or may not be in complex combination with a organophosphorus ligand as defined herein. Any suitable rhodium starting material may be employed, e.g. rhodium dicarbonyl acetylacetonate, $Rh_2O_3$, $Rh_4(CO)_{12}$, $Rh_6(CO)_{16}$, $Rh(NO_3)_3$, and organophosphorus ligand rhodium carbonyl hydrides. Carbonyl and organophosphorus ligands, if not already complexed with the initial rhodium, may be complexed to the rhodium either prior to or in situ during the process.

By way of illustration, the preferred catalyst precursor composition of this invention consists essentially of a solubilized rhodium carbonyl organophosphorus ligand complex precursor catalyst, a solvent and optionally free organophosphorus ligand prepared by forming a solution of rhodium dicarbonyl acetylacetonate, an organic solvent and a organophosphorus ligand as defined herein. The organophosphorus ligand readily replaces one of the carbonyl ligands of the rhodium acetylacetonate complex precursor at room temperature as witnessed by the evolution of carbon monoxide gas. This substitution reaction may be facilitated by heating the solution if desired. Any suitable organic solvent in which both the rhodium dicarbonyl acetylacetonate complex precursor and rhodium organophosphorus ligand complex precursor are soluble can be employed. The amounts of rhodium complex catalyst precursor, organic solvent and organophosphorus ligand, as well as their preferred embodiments present in such catalyst precursor compositions may obviously correspond to those amounts employable in the processes of this invention. Experience has shown that the acetylacetonate ligand of the precursor catalyst is replaced after the process, e.g., hydroformylation, has begun with a different ligand, e.g., hydrogen, carbon monoxide or organophosphorus ligand, to form the active complex catalyst as explained above. The acetylacetone which is freed from the precursor catalyst under hydroformylation conditions is removed from the reaction medium with the product aldehyde and thus is in no way detrimental to the hydroformylation process. The use of such preferred rhodium complex catalytic precursor compositions provides a simple economical and efficient method for handling the rhodium precursor rhodium and hydroformylation start-up.

Accordingly, the metal-organophosphorus ligand complex catalysts used in the processes of this invention consists essentially of the metal complexed with carbon monoxide, i.e., hydroformylation, and an organophosphorus ligand, said ligand being bonded (complexed) to the metal in a chelated and/or non-chelated fashion. Moreover, the terminology "consists essentially of", as used herein, does not exclude, but rather includes, hydrogen complexed with the metal, in addition to carbon monoxide and the organophosphorus ligand. Further, such terminology does not exclude the possibility of other organic ligands and/or anions that might also be complexed with the metal. Materials in amounts which unduly adversely poison or unduly deactivate the catalyst are not desirable and so the catalyst most desirably is free of contaminants such as metal-bound halogen (e.g., chlorine, and the like) although such may not be absolutely necessary. The hydrogen and/or carbonyl ligands of an active metal-organophosphorus ligand complex catalyst may be present as a result of being ligands bound to a precursor catalyst and/or as a result of in situ formation, e.g., due to the hydrogen and carbon monoxide gases employed in hydroformylation process of this invention.

As noted above, the organophosphorus ligands can be employed as both the ligand of the metal-organophosphorus ligand complex catalyst, as well as, the free organophosphorus ligand that can be present in the reaction medium of the processes of this invention. In addition, it is to be understood that while the organophosphorus ligand of the metal-organophosphorus ligand complex catalyst and any excess free organophosphorus ligand preferably present in a given process of this invention are normally the same type of ligand, different types of organophosphorus ligands, as well as, mixtures of two or more different organophosphorus ligands may be employed for each purpose in any given process, if desired.

The amount of metal-organophosphorus ligand complex catalyst present in the reaction medium of a given process of this invention need only be that minimum amount necessary to provide the given metal concentration desired to be employed and which will furnish the basis for at least that catalytic amount of metal necessary to catalyze the particular process desired. In general, metal concentrations in the range of from about 1 part per million to about 10,000 parts per million, calculated as free metal, and ligand to metal mole ratios in the catalyst solution ranging from about 1:1 or less to about 200:1 or greater, should be sufficient for most processes.

As noted above, in addition to the metal-organophosphorus ligand complex catalysts, the processes of this invention and especially the hydroformylation process can be carried out in the presence of free organophosphorus ligand. While the processes of this invention may be carried out in any excess amount of free organophosphorus ligand desired, the employment of free organophosphorus ligand may not be absolutely necessary. Accordingly, in general, amounts of ligand of from about 1.1 or less to about 100, or higher if desired, moles per mole of metal (e.g., rhodium) present in the reaction medium should be suitable for most purposes, particularly with regard to rhodium catalyzed hydroformylation; said amounts of ligand employed being the sum of both the amount of ligand that is bound (complexed) to the metal present and the amount of free (non-complexed) ligand present. Of course, if desired, make-up ligand can be supplied to the reaction medium of the process, at any time and in any suitable manner, to maintain a predetermined level of free ligand in the reaction medium.

As indicated above, the catalysts may be in heterogeneous form during the reaction and/or during the product separation. Such catalysts are particularly advantageous in the hydroformylation of olefins to produce high boiling or thermally sensitive aldehydes, so that the catalyst may be separated from the products by filtration or decantation at low temperatures. For example, the rhodium catalyst may be attached to a support so that the catalyst retains its solid form during both the hydroformylation and separation stages, or is soluble in a liquid reaction medium at high temperatures and then is precipitated on cooling.

As an illustration, the rhodium catalyst may be impregnated onto any solid support, such as inorganic oxides, (i.e. alumina, silica, titania, or zirconia) carbon, or ion exchange resins. The catalyst may be supported on, or intercalated inside the pores of, a zeolite, glass or clay; the catalyst may also be dissolved in a liquid film coating the pores of said zeolite or glass. Such zeolite-supported catalysts are particularly advantageous for producing one or more regioisomeric aldehydes in high selectivity, as determined by the pore size of the zeolite. The techniques for supporting catalysts on solids, such as incipient wetness, which will be known to those skilled in the art. The solid catalyst thus formed may still be complexed with one or more of the ligands defined above. Descriptions of such solid catalysts may be found in for example: J. Mol. Cat. 1991, 70, 363–368; Catal. Lett. 1991, 8, 209–214; J. Organomet. Chem, 1991, 403, 221–227; Nature, 1989, 339, 454–455; J. Catal. 1985, 96, 563–573; J. Mol. Cat. 1987, 39, 243–259.

The metal, e.g., rhodium, catalyst may be attached to a thin film or membrane support, such as cellulose acetate or polyphenylenesulfone, as described in for example J. Mol. Cat. 1990, 63, 213–221.

The metal, e.g., rhodium, catalyst may be attached to an insoluble polymeric support through an organophosphorus-containing ligand, such as an organophosphorus amide, incorporated into the polymer. The supported catalyst is not limited by the choice of polymer or phosphorus-containing species incorporated into it. Descriptions of polymer-supported catalysts may be found in for example: J. Mol. Cat. 1993, 83, 17–35; Chemtech 1983, 46; J. Am. Chem. Soc. 1987, 109, 7122–7127.

In the heterogeneous catalysts described above, the catalyst may remain in its heterogeneous form during the entire process and catalyst separation process. In another embodiment of the invention, the catalyst may be supported on a polymer which, by the nature of its molecular weight, is soluble in the reaction medium at elevated temperatures, but precipitates upon cooling, thus facilitating catalyst separation from the reaction mixture. Such "soluble" polymer-supported catalysts are described in for example: Polymer, 1992, 33, 161; J. Org. Chem. 1989, 54, 2726–2730.

More preferably, the hydroformylation reaction is carried out in the slurry phase due to the high boiling points of the products, and to avoid decomposition of the aldehyde products. The catalyst may then be separated from the product mixture, for example, by filtration or decantation. The reaction product fluid may contain a heterogeneous metal-organophosphorus ligand complex catalyst, e.g., slurry, or at least a portion of the reaction product fluid may contact a fixed heterogeneous metal-organophosphorus ligand complex catalyst during the particular process. In an embodiment of this invention, the metal-organophosphorus ligand complex catalyst may be slurried in the reaction product fluid.

The permissible reaction conditions employable in the processes of this invention are, of course, chosen depending on the particular syntheses desired. Such process conditions are well known in the art. All of the processes of this invention can be carried out in accordance with conventional procedures known in the art. Illustrative reaction conditions for conducting the processes of this invention are described, for example, in Kirk-Othmer, Encyclopedia of Chemical Technology, Fourth Edition, 1996, the pertinent portions of which are incorporated herein by reference. Depending on the particular process, operating temperatures may range from about −80° C. or less to about 500° C. or greater and operating pressures can range from about 1 psig or less to about 10,000 psig or greater.

The processes of this invention are conducted for a period of time sufficient to produce the desired products. The exact reaction time employed is dependent, in part, upon factors such as temperature, pressure, nature and proportion of starting materials, and the like. The reaction time will normally be within the range of from about one-half to about 200 hours or more, and preferably from less than about one to about 10 hours.

The processes of this invention and preferably the hydroformylation process may be conducted in the presence of an organic solvent for the metal-organophosphorus ligand complex catalyst. The solvent may also contain dissolved water up to the saturation limit. Depending on the particular catalyst and reactants employed, suitable organic solvents include, for example, alcohols, alkanes, alkenes, alkynes, ethers, aldehydes, ketones, esters, amides, amines, aromatics and the like. Any suitable solvent which does not unduly adversely interfere with the intended processes can be employed and such solvents may include those heretofore commonly employed in known metal catalyzed processes. Increasing the dielectric constant or polarity of a solvent may generally tend to favor increased reaction rates. Of course, mixtures of one or more different solvents may be employed if desired. It is obvious that the amount of solvent employed is not critical to the subject invention and need only be that amount sufficient to provide the reaction medium with the particular metal concentration desired for a given process. In general, the amount of solvent when employed may range from about 5 percent by weight up to about 99 percent by weight or more based on the total weight of the reaction mixture starting materials.

The processes of this invention are useful for preparing substituted and unsubstituted optically active and non-optically active compounds. Illustrative compounds prepared by the processes of this invention include, for example, substituted and unsubstituted alcohols or phenols; amines; amides; ethers or epoxides; esters; ketones; aldehydes; and nitriles. Illustrative of suitable optically active and non-optically active compounds which can be prepared by the processes of this invention (including starting material compounds as described hereinabove) include those permissible compounds which are described in Kirk-Othmer, Encyclopedia of Chemical Technology, Fourth Edition, 1996, the pertinent portions of which are incorporated herein by reference, and The Merck Index, An Encyclopedia of Chemicals, Drugs and Biologicals, Eleventh Edition, 1989, the pertinent portions of which are incorporated herein by reference.

The desired products of this invention may be recovered in any conventional manner and one or more separators or separation zones may be employed in any given process to recover the desired reaction product from its crude reaction product fluid. Suitable separation methods include, for example, solvent extraction, crystallization, distillation, vaporization, wiped film evaporation, falling film evaporation and the like. It may be desired to remove the products from the crude reaction mixture as they are formed through the use of trapping agents as described in published Patent Cooperation Treaty Patent Application WO 88/08835. A preferred method for separating the product mixtures from the other components of the crude reaction mixtures is by membrane separation. Such membrane separation can be achieved as set out in U.S. Pat. No. 5,430,194 and copending U.S. patent application Ser. No. 08/430,790, filed May 5, 1995, referred to above.

In an embodiment, the processes of this invention may be carried out by reacting one or more reactants in the presence of a metal-organopolyphosphorus ligand complex catalyst and optionally free organopolyphosphorus ligand to produce a reaction product fluid comprising one or more products, wherein said process is conducted at a carbon monoxide partial pressure such that reaction rate increases as carbon monoxide partial pressure decreases and reaction rate decreases as carbon monoxide partial pressure increases and which is sufficient to prevent and/or lessen deactivation of the metal-organopolyphosphorus ligand complex catalyst. See, for example, U.S. patent application Ser. No. 08/756,499, filed Nov. 26, 1996, the disclosure of which is incorporated herein by reference.

The processes of this invention may be carried out using, for example, a fixed bed reactor, a fluid bed reactor, a continuous stirred tank reactor (CSTR) or a slurry reactor. The optimum size and shape of the catalysts will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low. The at least one reaction zone employed in this invention may be a single vessel or may comprise two or more discreet vessels. The at least one separation zone employed in this invention may be a single vessel or may comprise two or more discrete vessels. The at least one scrubber zone employed in this invention may be a single vessel or may comprise two or more discrete vessels. The at least one acid removal zone employed in this invention may be a single vessel or may comprise two or more discreet vessels. It should be understood that the reaction zone(s) and separation zone(s) employed herein may exist in the same vessel or in different vessels. For example, reactive separation techniques such as reactive distillation, reactive membrane separation and the like may occur in the reaction zone(s).

The processes of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials. When complete conversion is not desired or not obtainable, the starting materials can be separated from the product, for example by distillation, and the starting materials then recycled back into the reaction zone.

The processes may be conducted in either glass lined, stainless steel or similar type reaction equipment. The reaction zone may be fitted with one or more internal and/or external heat exchangers) in order to control undue temperature fluctuations, or to prevent any possible "runaway" reaction temperatures.

The processes of this invention may be conducted in one or more steps or stages. The exact number of reaction steps or stages will be governed by the best compromise between capital costs and achieving high catalyst selectivity, activity, lifetime and ease of operability, as well as the intrinsic reactivity of the starting materials in question and the stability of the starting materials and the desired reaction product to the reaction conditions.

In an embodiment, the hydroformylation processes useful in this invention may be carried out in a multistaged reactor such as described, for example, in copending U.S. patent application Ser. No. 08/757,743, filed on Nov. 26, 1996, the disclosure of which is incorporated herein by reference. Such multistaged reactors can be designed with internal, physical barriers that create more than one theoretical reactive stage per vessel. In effect, it is like having a number of reactors inside a single continuous stirred tank reactor vessel. Multiple reactive stages within a single vessel is a cost effective way of using the reactor vessel volume. It significantly reduces the number of vessels that otherwise would be required to achieve the same results. Fewer vessels reduces the overall capital required and maintenance concerns with separate vessels and agitators.

Hydroformylation Processes

A preferred process useful in this invention is hydroformylation. Illustrative metal-organophosphorus ligand complex catalyzed hydroformylation processes which may experience such hydrolytic degradation of the organophosphorus ligand and catalytic deactivation include such processes as described, for example, in U.S. Pat. Nos. 4,148,830; 4,593,127; 4,769,498; 4,717,775; 4,774,361; 4,885,401; 5,264,616; 5,288,918; 5,360,938; 5,364,950; and 5,491,266; the disclosures of which are incorporated herein by reference. Accordingly, the hydroformylation processing techniques of this invention may correspond to any known processing techniques. Preferred process are those involving catalyst liquid recycle hydroformylation processes.

In general, such catalyst liquid recycle hydroformylation processes involve the production of aldehydes by reacting an olefinic unsaturated compound with carbon monoxide and hydrogen in the presence of a metal-organophosphorus ligand complex catalyst in a liquid medium that also contains an organic solvent for the catalyst and ligand. Preferably free organophosphorus ligand is also present in the liquid hydroformylation reaction medium. The recycle procedure generally involves withdrawing a portion of the liquid reaction medium containing the catalyst and aldehyde product from the hydroformylation reactor (i.e., reaction zone), either continuously or intermittently, and recovering the aldehyde product therefrom by use of a composite membrane such as disclosed in U.S. Pat. No. 5,430,194 and copending U.S. patent application Ser. No. 08/430,790, filed May 5, 1995, the disclosures of which are incorporated herein by reference, or by the more conventional and preferred method of distilling it (i.e., vaporization separation) in one or more stages under normal, reduced or elevated pressure, as appropriate, in a separate distillation zone, the non-volatilized metal catalyst containing residue being recycled to the reaction zone as disclosed, for example, in U.S. Pat. No. 5,288,918. Condensation of the volatilized materials, and separation and further recovery thereof, e.g., by further distillation, can be carried out in any conventional manner, the crude aldehyde product can be passed on for further purification and isomer separation, if desired, and any recovered reactants, e.g., olefinic starting material and syn gas, can be recycled in any desired manner to the hydroformylation zone (reactor). The recovered metal catalyst containing raffinate of such membrane separation or recovered non-volatilized metal catalyst containing residue of such vaporization separation can be recycled, to the hydroformylation zone (reactor) in any conventional manner desired.

In a preferred embodiment, the hydroformylation reaction product fluids employable herein includes any fluid derived from any corresponding hydroformylation process that contains at least some amount of four different main ingredients or components, i.e., the aldehyde product, a metal-organophosphorus ligand complex catalyst, free organophosphorus ligand and an organic solubilizing agent for said catalyst and said free ligand, said ingredients corresponding to those employed and/or produced by the hydroformylation process from whence the hydroformylation reaction mixture starting material may be derived. It is to be understood that the hydroformylation reaction mixture compositions employable herein can and normally will contain minor amounts of additional ingredients such as those which have either been deliberately employed in the hydroformylation process or formed in situ during said process. Examples of such ingredients that can also be present include unreacted olefin starting material, carbon monoxide and hydrogen gases, and in situ formed type products, such as saturated hydrocarbons and/or unreacted isomerized olefins corresponding to the olefin starting materials, and high boiling liquid aldehyde condensation byproducts, as well as other inert co-solvent type materials or hydrocarbon additives, if employed.

The substituted or unsubstituted olefin reactants that may be employed in the hydroformylation processes (and other suitable processes) of this invention include both optically active (prochiral and chiral) and non-optically active (achiral) oleflinic unsaturated compounds containing from 2 to 40, preferably 4 to 20, carbon atoms. Such olefinic unsaturated compounds can be terminally or internally unsaturated and be of straight-chain, branched chain or cyclic structures, as well as olefin mixtures, such as obtained from the oligomerization of propene, butene, isobutene, etc. (such as so called dimeric, trimeric or tetrameric propylene and the like, as disclosed, for example, in U.S. Pat. Nos. 4,518,809 and 4,528,403). Moreover, such olefin compounds may further contain one or more ethylenic unsaturated groups, and of course, mixtures of two or more different olefinic unsaturated compounds may be employed as the starting material if desired. For example, commercial alpha olefins containing four or more carbon atoms may contain minor amounts of corresponding internal olefins and/or their corresponding saturated hydrocarbon and that such commercial olefins need not necessarily be purified from same prior to being reacted. Illustrative mixtures of olefinic starting materials that can be employed in the hydroformylation reactions include, for example, mixed butenes, e.g., Raffinate I and II. Further such olefinic unsaturated compounds and the corresponding products derived therefrom may also contain one or more groups or substituents which do not unduly adversely affect the processes of this invention such as described, for example, in U.S. Pat. Nos. 3,527,809, 4,769,498 and the like.

Most preferably the subject invention is especially useful for the production of non-optically active aldehydes, by hydroformylating achiral alpha-olefins containing from 2 to 30, preferably 4 to 20, carbon atoms, and achiral internal olefins containing from 4 to 20 carbon atoms as well as starting material mixtures of such alpha olefins and internal olefins.

Illustrative alpha and internal olefins include, for example, ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, 2-octene, cyclohexene, propylene dimers, propylene trimers, propylene tetramers, 2-ethyl-1-hexene, styrene, 4-methyl styrene, 4-isopropyl styrene, 4-tert-butyl styrene, alpha-methyl styrene, 4-tert-butyl-alpha-methyl styrene, 1,3-diisopropenylbenzene, 3-phenyl-1-propene, 1,4-hexadiene, 1,7-octadiene, 3-cyclohexyl-1-butene, and the like, as well as, 1,3-dienes, butadiene, piperylene, isoprene, alkyl alkenoates, e.g., methyl pentenoate, alkenyl alkanoates, alkenyl alkyl ethers, alkenols, e.g., pentenols, alkenals, e.g., pentenals, and the like, such as allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, n-propyl-7-octenoate, 3-butenenitrile, 5-hexenamide, eugenol, iso-eugenol, safrole, iso-safrole, anethol, 4-allylanisole, indene, limonene, beta-pinene, dicyclopentadiene, cyclooctadiene, camphene, linalool, and the like.

Illustrative prochiral and chiral olefins useful in the asymmetric hydroformylation processes (and other asymmetric processes) that can be employed to produce enantiomeric product mixtures that may be encompassed by in this invention include those represented by the formula:

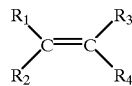

(XII)

wherein $R_1$, $R_2$, $R_3$ and $R_4$ are the same or different (provided $R_1$ is different from $R_2$ or $R_3$ is different from $R_4$) and are selected from hydrogen; alkyl; substituted alkyl, said substitution being selected from dialkylamino such as benzylamino and dibenzylamino, alkoxy such as methoxy and ethoxy, acyloxy such as acetoxy, halo, nitro, nitrile, thio, carbonyl, carboxamide, carboxaldehyde, carboxyl, carboxylic ester; aryl including phenyl; substituted aryl including phenyl, said substitution being selected from alkyl, amino including alkylamino and dialkylamino such as benzylamino and dibenzylamino, hydroxy, alkoxy such as methoxy and ethoxy, acyloxy such as acetoxy, halo, nitrile, nitro, carboxyl, carboxaldehyde, carboxylic ester, carbonyl, and thio; acyloxy such as acetoxy; alkoxy such as methoxy and ethoxy; amino including alkylamino and dialkylamino such as benzylamino and dibenzylamino; acylamino and diacylamino such as acetylbenzylamino and diacetylamino; nitro; carbonyl; nitrile; carboxyl; carboxamide; carboxaldehyde; carboxylic ester; and alkylmercapto such as methylmercapto. It is understood that the prochiral and chiral olefins of this definition also include molecules of the above general formula where the R groups are connected to form ring compounds, e.g., 3-methyl-1-cyclohexene, and the like.

Illustrative optically active or prochiral olefinic compounds useful in asymmetric hydroformylation processes (and other asymmetric processes) of this invention include, for example, p-isobutylstyrene, 2-vinyl-6-methoxy-2-naphthylene, 3-ethenylphenyl phenyl ketone, 4-ethenylphenyl-2-thienylketone, 4-ethenyl-2-fluorobiphenyl, 4-(1,3-dihydro-1-oxo-2H-isoindol-2-yl) styrene, 2-ethenyl-5-benzoylthiophene, 3-ethenylphenyl phenyl ether, propenylbenzene, isobutyl-4-propenylbenzene, phenyl vinyl ether and the like. Other olefinic compounds include substituted aryl ethylenes as described, for example, in U.S. Pat. Nos. 4,329,507, 5,360, 938 and 5,491,266, the disclosures of which are incorporated herein by reference.

Illustrative of suitable substituted and unsubstituted olefinic starting materials include those permissible substituted and unsubstituted olefinic compounds described in Kirk-Othmer, Encyclopedia of Chemical Technology, Fourth Edition, 1996, the pertinent portions of which are incorporated herein by reference.

As noted, the hydroformylation processes of this invention involve the use of a metal-organophosphorus ligand complex catalyst as described hereinabove. The hydroformylation catalysts may be in homogeneous or heterogeneous form during the reaction and/or during the product separation. Of course mixtures of such catalysts can also be employed if desired. The amount of metal-organophosphorus ligand complex catalyst present in the reaction medium of a given hydroformylation process encompassed by this invention need only be that minimum amount necessary to provide the given metal concentration desired to be employed and which will furnish the basis for at least the catalytic amount of metal necessary to catalyze the particular hydroformylation process involved such as disclosed, for example, in the above-mentioned patents. In general, metal, e.g., rhodium, concentrations in the range of from about 10 parts per million to about 1000 parts per million, calculated as free rhodium, in the hydroformylation reaction medium should be sufficient for most processes, while it is generally preferred to employ from about 10 to 500 parts per million of metal, e.g., rhodium, and more preferably from 25 to 350 parts per million of metal, e.g., rhodium.

In addition to the metal-organophosphorus ligand complex catalyst, free organophosphorus ligand (i.e., ligand that is not complexed with the metal) may also be present in the hydroformylation reaction medium. The free organophosphorus ligand may correspond to any of the above-defined organophosphorus ligands employable herein. It is preferred that the free organophosphorus ligand be the same as the organophosphorus ligand of the metal-organophosphorus ligand complex catalyst employed. However, such ligands need not be the same in any given process. The hydroformylation process of this invention may involve from about 0.1 moles or less to about 100 moles or higher, of free organophosphorus ligand per mole of metal in the hydroformylation reaction medium. Preferably the hydroformylation process of this invention is carried out in the presence of from about 1 to about 50 moles of organophosphorus ligand, and more preferably for organopolyphosphorus ligands from about 1.1 to about 4 moles of organopolyphosphorus ligand, per mole of metal present in the reaction medium; said amounts of organophosphorus ligand being the sum of both the amount of organophosphorus ligand that is bound (complexed) to the metal present and the amount of free (non-complexed) organophosphorus ligand present. Since it is more preferred to produce non-optically active aldehydes by hydroformylating achiral olefins, the more preferred organophosphorus ligands are achiral type organophosphorus ligands, especially those encompassed by Formula (V) above, and more preferably those of Formulas (VI) and (IX) above. Of course, if desired, make-up or additional organophosphorus ligand can be supplied to the reaction medium of the hydroformylation process at any time and in any suitable manner, e.g. to maintain a predetermined level of free ligand in the reaction medium.

The reaction conditions of the hydroformylation processes encompassed by this invention may include any suitable type hydroformylation conditions heretofore employed for producing optically active and/or non-optically active aldehydes. For instance, the total gas pressure of hydrogen, carbon monoxide and olefin starting compound of the hydroformylation process may range from about 1 to about 10,000 psia. In general, however, it is preferred that the process be operated at a total gas pressure of hydrogen, carbon monoxide and olefin starting compound of less than about 2000 psia and more preferably less than about 500 psia. The minimum total pressure is limited predominantly by the amount of reactants necessary to obtain a desired rate of reaction. More specifically the carbon monoxide partial pressure of the hydroformylation process of this invention is preferable from about 1 to about 1000 psia, and more preferably from about 3 to about 800 psia, while the hydrogen partial pressure is preferably about 5 to about 500 psia and more preferably from about 10 to about 300 psia. In general $H_2$:CO molar ratio of gaseous hydrogen to carbon monoxide may range from about 1:10 to 100:1 or higher, the more preferred hydrogen to carbon monoxide molar ratio being from about 1:10 to about 10:1. Further, the hydroformylation process may be conducted at a reaction temperature from about −25° C. to about 200° C. In general hydroformylation reaction temperatures of about 50° C. to about 120° C. are preferred for all types of olefinic starting materials. Of course it is to be understood that when non-optically active aldehyde products are desired, achiral type olefin starting materials and organophosphorus ligands are employed and when optically active aldehyde products are desired prochiral or chiral type olefin starting materials and organophosphorus ligands are employed. Of course, it is to be also understood that the hydroformylation reaction conditions employed will be governed by the type of aldehyde product desired.

The hydroformylation processes encompassed by this invention are also conducted in the presence of an organic solvent for the metal-organophosphorus ligand complex catalyst and free organophosphorus ligand. The solvent may also contain dissolved water up to the saturation limit. Depending on the particular catalyst and reactants employed, suitable organic solvents include, for example, alcohols, alkanes, alkenes, alkynes, ethers, aldehydes, higher boiling aldehyde condensation byproducts, ketones, esters, amides, tertiary amines, aromatics and the like. Any suitable solvent which does not unduly adversely interfere with the intended hydroformylation reaction can be employed and such solvents may include those disclosed heretofore commonly employed in known metal catalyzed hydroformylation reactions. Mixtures of one or more different solvents may be employed if desired. In general, with regard to the production of achiral (non-optically active) aldehydes, it is preferred to employ aldehyde compounds corresponding to the aldehyde products desired to be produced and/or higher boiling aldehyde liquid condensation byproducts as the main organic solvents as is common in the art. Such aldehyde condensation byproducts can also be preformed if desired and used accordingly. Illustrative preferred solvents employable in the production of aldehydes include ketones (e.g. acetone and methylethyl ketone), esters (e.g. ethyl acetate), hydrocarbons (e.g. toluene), nitrohydrocarbons (e.g. nitrobenzene), ethers (e.g. tetrahydrofuran (THF) and sulfolane. Suitable solvents are disclosed in U.S. Pat. No. 5,312,996. The amount of solvent employed is not critical to the subject invention and need only be that amount sufficient to solubilize the catalyst and free ligand of the hydroformylation reaction mixture to be treated. In general, the amount of solvent may range from about 5 percent by weight up to about 99 percent by weight or more based on the total weight of the hydroformylation reaction mixture starting material.

Accordingly illustrative non-optically active aldehyde products include e.g., propionaldehyde, n-butyraldehyde, isobutyraldehyde, n-valeraldehyde, 2-methyl 1-butyraldehyde, hexanal, hydroxyhexanal, 2-methyl valeraldehyde, heptanal, 2-methyl 1-hexanal, octanal, 2-methyl 1-heptanal, nonanal, 2-methyl-1-octanal, 2-ethyl 1-heptanal, 3-propyl 1-hexanal, decanal, adipaldehyde, 2-methylglutaraldehyde, 2-methyladipaldehyde, 3-methyladipaldehyde, 3-hydroxypropionaldehyde, 6-hydroxyhexanal, alkenals, e.g., 2-, 3- and 4-pentenal, alkyl 5-formylvalerate, 2-methyl-1-nonanal, undecanal, 2-methyl 1-decanal, dodecanal, 2-methyl 1-undecanal, tridecanal, 2-methyl 1-tridecanal, 2-ethyl, 1-dodecanal, 3-propyl-1-undecanal, pentadecanal, 2-methyl-1-tetradecanal, hexadecanal, 2-methyl-1-pentadecanal, heptadecanal, 2-methyl-1-hexadecanal, octadecanal, 2-methyl-1-heptadecanal, nonodecanal, 2-methyl-1-octadecanal, 2-ethyl 1-heptadecanal, 3-propyl-1-hexadecanal, eicosanal, 2-methyl-1-nonadecanal, heneicosanal, 2-methyl-1-eicosanal, tricosanal, 2-methyl1-docosanal, tetracosanal, 2-methyl-1-tricosanal, pentacosanal, 2-methyl-1-tetracosanal, 2-ethyl 1-tricosanal, 3-propyl-1-docosanal, heptacosanal, 2-methyl-1-octacosanal, nonacosanal, 2-methyl-1-octacosanal, hentriacontanal, 2-methyl-1-triacontanal, and the like.

Illustrative optically active aldehyde products include (enantiomeric) aldehyde compounds prepared by the asymmetric hydroformylation process of this invention such as, e.g. S-2-(p-isobutylphenyl)-propionaldehyde, S-2-(6-methoxy-2-naphthyl)propionaldehyde, S-2-(3-benzoylphenyl)-propionaldehyde, S-2-(p-thienoylphenyl) propionaldehyde, S-2-(3-fluoro-4-phenyl) phenylpropionaldehyde, S-2-[4-(1,3-dihydro-1-oxo-2H-isoindol-2-yl)phenyl]propionaldehyde, S-2-(2-methylacetaldehyde)-5-benzoylthiophene and the like.

Illustrative of suitable substituted and unsubstituted aldehyde products include those permissible substituted and unsubstituted aldehyde compounds described in Kirk-Othmer, Encyclopedia of Chemical Technology, Fourth Edition, 1996, the pertinent portions of which are incorporated herein by reference.

As indicated above, it is generally preferred to carry out the hydroformylation processes of this invention in a continuous manner. In general, continuous hydroformylation processes are well known in the art and may involve: (a) hydroformylating the olefinic starting material(s) with carbon monoxide and hydrogen in a liquid homogeneous reaction mixture comprising a solvent, the metal-organophosphorus ligand complex catalyst, and free organophosphorus ligand; (b) maintaining reaction temperature and pressure conditions favorable to the hydroformylation of the olefinic starting material(s); (c) supplying make-up quantities of the olefinic starting material(s), carbon monoxide and hydrogen to the reaction medium as those reactants are used up; and (d) recovering the desired aldehyde hydroformylation product(s) in any manner desired. The continuous process can be carried out in a single pass mode, i.e., wherein a vaporous mixture comprising unreacted olefinic starting material(s) and vaporized aldehyde product is removed from the liquid reaction mixture from whence the aldehyde product is recovered and make-up olefinic starting material(s), carbon monoxide and hydrogen are supplied to the liquid reaction medium for the next single pass through without recycling the unreacted olefinic starting material(s). Such types of recycle procedure are well known in the art and may involve the liquid recycling of the metal-organophosphorus ligand complex catalyst fluid separated from the desired aldehyde reaction product(s), such as disclosed, for example, in U.S. Pat. No. 4,148,830 or a gas recycle procedure such as disclosed, for example, in U.S. Pat. No. 4,247,486, as well as a combination of both a liquid and gas recycle procedure if desired. The disclosures of said U.S. Pat. Nos. 4,148,830 and 4,247,486 are incorporated herein by reference thereto. The most preferred hydroformylation process of this invention comprises a continuous liquid catalyst recycle process. Suitable liquid catalyst recycle procedures are disclosed, for example, in U.S. Pat. Nos. 4,668,651; 4,774,361; 5,102,505 and 5,110,990.

In an embodiment of this invention, the aldehyde product mixtures may be separated from the other components of the crude reaction mixtures in which the aldehyde mixtures are produced by any suitable method. Suitable separation methods include, for example, solvent extraction, phase separation, crystallization, distillation, vaporization, wiped film evaporation, falling film evaporation and the like. It may be desired to remove the aldehyde products from the crude reaction mixture as they are formed through the use of trapping agents as described in published Patent Cooperation Treaty Patent Application WO 88/08835. A preferred method for separating the aldehyde mixtures from the other components of the crude reaction mixtures is by membrane separation. Such membrane separation can be achieved as set out in U.S. Pat. No. 5,430,194 and copending U.S. patent application Ser. No. 08/430,790, filed May 5, 1995, referred to above.

As indicated above, at the conclusion of (or during) the process of this invention, the desired aldehydes may be recovered from the reaction mixtures used in the process of this invention. For example, the recovery techniques disclosed in U.S. Pat. Nos. 4,148,830 and 4,247,486 can be used. For instance, in a continuous liquid catalyst recycle process the portion of the liquid reaction mixture (containing aldehyde product, catalyst, etc.), i.e., reaction product fluid, removed from the reaction zone can be passed to a separation zone, e.g., vaporizer/separator, wherein the desired aldehyde product can be separated via distillation, in one or more stages, under normal, reduced or elevated pressure, from the liquid reaction fluid, condensed and collected in a product receiver, and further purified if desired. The remaining non-volatilized catalyst containing liquid reaction mixture may then be recycled back to the reaction zone as may if desired any other volatile materials, e.g., unreacted olefin, together with any hydrogen and carbon monoxide dissolved in the liquid reaction after separation thereof from the condensed aldehyde product, e.g., by distillation in any conventional manner. In general, it is preferred to separate the desired aldehydes from the catalyst-containing reaction mixture under reduced pressure and at low temperatures so as to avoid possible degradation of the organophosphorus ligand and reaction products. When an alpha-mono-olefin reactant is also employed, the aldehyde derivative thereof can also be separated by the above methods.

More particularly, distillation and separation of the desired aldehyde product from the metal-organophosphorus ligand complex catalyst containing reaction product fluid may take place at any suitable temperature desired. In general, it is recommended that such distillation take place at relatively low temperatures, such as below 150° C., and more preferably at a temperature in the range of from about 50° C. to about 140° C. It is also generally recommended that such aldehyde distillation take place under reduced pressure, e.g., a total gas pressure that is substantially lower than the total gas pressure employed during hydroformylation when low boiling aldehydes (e.g., $C_4$ to $C_6$) are involved or under vacuum when high boiling aldehydes (e.g. $C_7$ or greater) are involved. For instance, a common practice is to subject the liquid reaction product medium removed from the hydroformylation reaction zone to a pressure reduction so as to volatilize a substantial portion of the unreacted gases dissolved in the liquid medium which now contains a much lower synthesis gas concentration than was present in the hydroformylation reaction medium to the distillation zone, e.g. vaporizer/separator, wherein the desired aldehyde product is distilled. In general, distillation pressures ranging from vacuum pressures on up to total gas pressure of about 50 psig should be sufficient for most purposes.

Water and Acid Removal Treatment

As stated above, the subject invention resides in the discovery that hydrolytic decomposition and rhodium catalyst deactivation as discussed herein can be prevented or lessened by treating at least a portion of the reaction product fluid derived from the process and which also contains phosphorus acidic compounds formed during said process with one or more acid removal substances sufficient to remove at least some amount of the phosphorus acidic compounds from said reaction product fluid. Because metal salt contaminants, e.g., iron, zinc, calcium salts and the like, in a reaction product fluid undesirably promote the self condensation of aldehydes, an advantage of this invention is that one can use the acidity removing capability of certain acid removal substances with minimal transfer of metal salts to the reaction product fluid. The use of one or more acid removal substances for removing phosphorus acidic compounds formed in metal-organophosphorus ligand complex catalyzed processes in order to prevent and/or lessen hydrolytic degradation of the organophosphorus ligand and deactivation of the metal-organophosphorus ligand complex catalyst of such processes is disclosed in copending U.S. patent application Ser. No. 08/757,742, filed on Nov. 26, 1996, the disclosure of which is incorporated herein by reference.

The removal of at least some amount of the phosphorus acid compounds, for example, $H_3PO_3$, aldehyde acids such as hydroxy alkyl phosphonic acids, $H_3PO_4$ and the like, from the reaction, e.g., hydroformylation, system allows one to control the acidity of the reaction medium, thereby stabilizing the useful organophosphorus ligand by preventing or lessening its hydrolytic decomposition. The need to control the acidity in organophosphorus ligand promoted metal catalyzed hydroformylation was explained above. Thus the purpose of the subject invention is to remove or reduce excessive acidity from the catalyst system in order to maintain a proper acidity level in the reaction product fluid so that the consumption of the useful organophosphorus ligands do not hydrolytically degrade at an unacceptable rate while keeping catalyst activity at a productive level. The subject invention submits that the best means for regulating such acidity is to remove such phosphorus acidic materials from the reaction product fluid in one or more acid removal zones containing one or more acid removal substances. In this way the acidic materials are removed as disclosed herein as opposed to merely being scavenged and/or neutralized and allowed to remain in the reaction medium, thereby avoiding accumulation of such scavenged and/or neutralized byproducts, and preventing further possible necessary secondary chemistry or the building of salt deposits in the reactor zone, separator zone and/or scrubber zone.

Said treatment of the metal-organophosphorus ligand complex catalyst containing reaction product fluid with the water may be conducted in any suitable manner or fashion desired that does not unduly adversely affect the basic process from which said reaction product fluid was derived. For instance, the water treatment may be conducted on all or any portion of the desired reaction product fluid that is to be treated and which has been removed from the at least one reaction zone or the at least one separation zone. The treated contacted water may then be sent to the one or more acid removal zones or returned to the at least one reaction zone or the at least one separation zone. Alternately, water may be sprayed into or otherwise added to the at least one reaction zone or the at least one separation zone to achieve acidity control. The water layer formed may then be decanted from the reaction product fluid.

This invention involving the use of water is especially adaptable for use in continuous liquid catalyst recycle hydroformylation processes that employ the invention of U.S. Pat. No. 5,288,918, which comprises carrying out the process in the presence of a catalytically active enhancing additive, said additive being selected from the class consisting of added water, a weakly acidic compound (e.g., biphenol), or both added water and a weakly acidic compound. The enhancing additive is employed to help selectively hydrolyze and prevent the build-up of an undesirable monophosphorus byproduct that can be formed during certain processes and which poisons the metal catalyst as explained therein. Nonetheless, it is to be understood that a preferred process of this invention, i.e., the embodiment comprising preventing and/or lessening hydrolytic degradation of the organophosphorus ligand and deactivation of the metal-organophosphorus ligand complex catalyst by (a) treating in at least one scrubber zone at least a portion of the reaction product fluid derived from said hydroformylation process and which also contains phosphorus acidic compounds formed during said process with water sufficient to remove at least some amount of the phosphorus acidic compounds from said reaction product fluid and (b) treating in at least one acid removal zone at least a portion of the water which contains phosphorus acidic compounds removed from said reaction product fluid with one or more acid removal substances sufficient to remove at least some amount of the phosphorus acidic compounds from said water, is still considered to be essentially a "non-aqueous" process, which is to say, any water present in the reaction medium is not present in an amount sufficient to cause either the reaction or said medium to be considered as encompassing a separate aqueous or water phase or layer in addition to an organic phase.

Also, it is to be understood that another preferred process of this invention, i.e., the embodiment comprising preventing and/or lessening hydrolytic degradation of the organophosphorus ligand and deactivation of the metal-organophosphorus ligand complex catalyst by treating at least a portion of the reaction product fluid derived from the process and which also contains phosphorus acidic compounds formed during said process by introducing one or more acid removal substances into said at least one reaction zone and/or said at least one separation zone sufficient to remove at least some amount of the phosphorus acidic compounds from said reaction product fluid, is also considered to be essentially a "non-aqueous" process.

Thus, for example, water may be used to treat all or part of a reaction product fluid of a continuous liquid catalyst recycle hydroformylation process that has been removed from the reaction zone at any time prior to or after separation of the aldehyde product therefrom. More preferably said water treatment involves treating all or part of the reaction product fluid obtained after distillation of as much of the aldehyde product desired, for example, prior to or during the recycling of said reaction product fluid to the reaction zone. For instance, a preferred mode would be to continuously pass all or part (e.g. a slip stream) of the recycled reaction product fluid that is being recycled to the reaction zone through a liquid extractor containing the water just before said catalyst containing residue is to re-enter the reaction zone.

Thus it is to be understood that the metal-organophosphorus ligand complex catalyst containing reaction product fluid to be treated with water may contain in addition to the catalyst complex and its organic solvent, product, free organophosphorus ligand, unreacted reactants, and any other ingredient or additive consistent with the reaction medium of the process from which said reaction product fluids are derived.

Moreover, removal of the desired product can cause concentrations of the other ingredients of the reaction product fluids to be increased proportionately. Thus for example, the organophosphorus ligand concentration in the metal-organophosphorus ligand complex catalyst containing reaction product fluid to be treated by water in accordance with the process of this invention may range from between about 0.005 and 15 weight percent based on the total weight of the reaction product fluid. Preferably the ligand concentration is between 0.01 and 10 weight percent, and more preferably is between about 0.05 and 5 weight percent on that basis. Similarly, the concentration of the metal in the metal-organophosphorus ligand complex catalyst containing reaction product fluid to be treated by the water in accordance with the process of this invention may be as high as about 5000 parts per million by weight based on the weight of the reaction product fluid. Preferably the metal concentration is between about 50 and 2500 parts per million by weight based on the weight of the reaction product fluid, and more preferably is between about 70 and 2000 parts per million by weight based on the weight of the reaction product fluid.

The manner in which the metal-organophosphorus ligand complex catalyst containing reaction product fluid and water are contacted, as well as such treatment conditions, as the amount of water, temperature, pressure and contact time are not narrowly critical and obviously need only be sufficient to obtain the results desired. For instance, said treatment may be carried out in any suitable vessel or container, e.g. any conventional liquid extractor, which provides a suitable means for thorough contact between the organic reaction product fluid and water, may be employed herein. In general it is preferred to pass the organic reaction product fluid through the water in a sieve tray extractor column in a counter-current fashion. The amount of water employed by the subject invention and time of contact with the reaction product fluid need only be that which is sufficient to remove at least some amount of the phosphorus acidic compounds which cause hydrolytic degradation of the desirable organophosphorus ligands. Preferably the amount of water is sufficient to at least maintain the concentration of such acidic compounds below the threshold level that causes rapid degradation of the organophosphorus ligand.

For instance, a preferred quantity of water is the quantity which ensures that any degradation of the organophosphorus ligand proceeds by the "non-catalytic mechanism" as described in "The Kinetic Rate Law for Autocatalytic Reactions" by Mata-Perez et al., Journal of Chemical Education, Vol. 64, No. 11, November 1987, pages 925 to 927, rather than by the "catalytic mechanism" described in said article. Typically maximum water concentrations are only governed by practical considerations. As noted, treatment conditions such as temperature, pressure and contact time may also vary greatly and any suitable combination of such conditions may be employed herein. For instance, a decrease in one of such conditions may be compensated for by an increase in one or both of the other conditions, while the opposite correlation is also true. In general liquid temperatures ranging from about 10° C. to about 120° C., preferably from about 20° C. to about 80° C., and more preferably from about 25° C. to about 60° C. should be suitable for most instances, although lower or higher temperatures could be employed if desired. As noted above, it has been surprisingly discovered that minimum loss of organophosphorus ligand occurs when a reaction product fluid containing a metal-organophosphorus ligand complex catalyst is contacted with the acid removal substances or is contacted with water and the contacted water thereafter treated with the acid removal substances even at elevated temperatures. Normally the treatment is carried out under pressures ranging from ambient to reaction pressures and the contact time may vary from a matter of seconds or minutes to a few hours or more.

Moreover, success in removing phosphorus acidic compounds from the reaction product fluid according to the subject invention may be determined by measuring the rate degradation (consumption) of the organophosphorus ligand present in the reaction medium. The consumption rate can vary over a wide range, e.g., from about $\leq 0.6$ up to about 5 grams per liter per day, and will be governed by the best compromise between cost of ligand and treatment frequency to keep hydrolysis below autocatalytic levels. Preferably the acid removal substance and water treatment of this invention is carried out in such a manner that the consumption of the desired organophosphorus ligand present in the reaction medium of the process is maintained at an acceptable rate, e.g., $\leq 0.5$ grams of ligand per liter per day, and more preferably $\leq 0.1$ grams of ligand per liter per day, and most preferably $\leq 0.06$ grams of ligand per liter per day. As the neutralization and extraction of phosphorus acidic compounds into the water proceeds, the pH of the water will decrease and become more and more acidic. When the water reaches an unacceptable acidity level it may simply be replaced with new water.

A preferred method of operation of this invention is to pass all or a portion of the reaction product fluid before aldehyde removal or reaction product fluid concentration after removal of aldehyde through the water and the contacted water through one or more acid removal substance beds. Alternately, water may be sprayed into or otherwise added to the at least one reaction zone or the at least one separation zone to achieve acidity control. The water layer formed may then be separated, e.g., decanted, from the reaction product fluid and sent to the one or more acid removal substance beds. An advantage of this scheme is that extraction capability is immediately available if acidity forms in the reaction product fluid. This invention is not intended to be limited in any manner by the permissible means for contacting a reaction product fluid with water or water with an acid removal substance (either inside or outside of the reaction zone, separation zone, scrubber zone or acid removal zone).

For purposes of this invention, "non-contacted water" is contemplated to include water that has not been contacted with the reaction product fluid and "contacted water" is contemplated to include water that has been contacted with the reaction product fluid and/or acid removal substances.

Any means to prepare the non-contacted water for use with the process of this invention can be used so long as the water is substantially free of catalyst poisons, inhibitors, or compounds that would promote undesirable side reactions in the catalyst solution. A summary of water treatment techniques can be found in the Kirk Othmer, Encyclopedia of Chemical Technology, Fourth Edition, 1996.

Water treatment should begin with an evaluation of the water quality needs for the process. For acid extraction from reaction product fluids containing metal-organophosphorus ligand complex catalysts, the quality of water required is generally of boiler quality or better. Sources of water for purification can vary greatly in purity from river water containing logs, silt and other debris, to steam condensate that is relatively pure. If river water is to be used, purification starts with filtration of the largest pieces. Grates or screens may be used for this first filtration step. A number of techniques can be used to remove other solids that may be present in the water including; sedimentation, centrifugal separation, filtration, coagulation, flocculation, magnetic separation, or combinations of these. After clarified water is obtained, the remaining dissolved solids can also be treated in a number of ways. Distillation is still commonly practiced. Dissolved salts may be treated with other acids or bases to precipitate certain compounds. The acids or bases that are added are chosen based on the solubility of the compounds that will be produced. Ion exchange is another popular method for removing dissolved salts. The most common ion exchange method uses sodium as the cation. Other ion exchange techniques with protons or hydroxide ions may also be employed. Adsorption can be used to remove some metal salts and organic compounds that may be present. Activated carbon is used commonly as an adsorbent. Membranes are still another technique that may be used removed dissolved salts or other colloidal particles. Membranes separate based on size, electronic charge, hydrophobicity, or other physical-chemical property differences. Reverse osmosis is an example of using membranes to purify water. If dissolved gases such as oxygen are present, the water can be stripped with steam or nitrogen or subjected to vacuum to remove or replace the dissolved gas. A preferred process to purify non-contacted water necessary for the acid removal would be a combination of some of the aforementioned techniques.

Internal techniques where additives are used to counteract the harmful effects of impurities can also be used to prepare non-contacted water for use in extraction, but the external techniques described in the preceding paragraph are more preferred.

The contacted water employable in this invention may comprise any suitable water such that the pH of the contacted water may range from about 2 to about 12, preferably from about 2.5 to about 11 and more preferably from about 3 to about 10. The flowrate of water through the extractor and/or the addition of water to the at least one reaction zone and/or the at least one separation zone should be sufficient to control pH of the water at desired levels. An increased flowrate of water through the extractor may cause removal, i.e., through the water effluent, of certain amounts of one or more aldehyde products from the process.

In a preferred embodiment of this invention, one or more aldehyde products removed by water extraction can be recovered and returned to the process as depicted in the process flow diagram of FIG. 1. For example, the one or more aldehyde products may be returned to the hydroformylation process by steam stripping the water effluent from the extractor and returning the organic phase of the condensed stripper heads to the hydroformylation process. The aqueous phase of the stripper heads may be returned to the stripper feed. The tails of the stripper may contain the acidic decomposition products from the catalyst.

Said treatment of the water containing phosphorus acidic compounds removed from the reaction product fluid with the one or more acid removal substances may be conducted in any suitable manner or fashion desired that does not unduly adversely affect the basic process from which said reaction product fluid was derived. For instance, the acid removal treatment may be conducted on all or any portion of the water that is to be treated and which has been removed from the at least one scrubber zone. The treated water may then be returned to the at least one scrubber zone. Alternately, water may be sprayed into or otherwise added to the at least one reaction zone or the at least one separation zone to achieve acidity control. The water layer formed may then be separated, e.g., decanted, from the reaction product fluid and treated with one or more acid removal substances to remove the phosphorus acidic compounds. The treated water may then be returned to the at least one reaction zone or the at least one separation zone.

The manner in which the water containing phosphorus acidic compounds removed from the reaction product fluid and the one or more acid removal substances are contacted, as well as such treatment conditions, as the amount of water, the number and type of acid removal substances, temperature, pressure and contact time are not narrowly critical and obviously need only be sufficient to obtain the results desired. For instance, said treatment may be carried out in any suitable vessel or container which provides a suitable means for thorough contact between the water and one or more acid removal substances, may be employed herein. The amount of water and acid removal substances employed by the subject invention and time of contact need only be that which is sufficient to remove at least some amount of the phosphorus acidic compounds which cause hydrolytic degradation of the desirable organophosphorus ligands. Preferably the amount of water and acid removal substances is sufficient to at least maintain the concentration of such phosphorus acidic compounds below the threshold level that causes rapid degradation of the organophosphorus ligand. Also, preferably, the fraction of water sent from the scrubber zone to the acid removal zone may be controlled based on the pH of the water in the scrubber zone.

The treatment of the reaction product fluid with one or more acid removal substances may be conducted in any suitable manner or fashion desired that does not unduly adversely affect the basic process from which said reaction product fluid was derived. For instance, the acid removal treatment may be conducted on all or any portion of the reaction product fluid that is to be treated and which has been removed from the at least one reaction zone or at least one separation zone. The treated reaction product fluid may then be returned to the at least one reaction zone or at least one separation zone. Alternately, acid removal substances, e.g., calcium carbonate powder, may be added to the at least one reaction zone or the at least one separation zone to achieve acidity control. The precipitate formed may then be removed from the at least one reaction zone or the at least one separation zone.

The acid removal substances employed should have limited solubility in the water which contains phosphorus acidic compounds removed from the reaction product fluid. In the broad practice of this invention, by "insoluble" we mean insoluble at temperatures employed in the practice of this invention.

Illustrative acid removal substances useful in this invention include, for example, metal oxides, hydroxides, carbonates, bicarbonates and carboxylates. Preferred acid removal substances include carbonates such as calcium carbonate. The acid removal substances useful in this invention are not narrowly critical and can be any compounds capable of effectively removing such phosphorus acidic compounds formed in metal-organophosphorus ligand complex catalyzed processes and thereby preventing and/or lessening hydrolytic degradation of organophosphorus ligands and deactivation of metal-organophosphorus ligand complex catalysts that may occur over the course of time during processes which employ metal-organophosphorus ligand complex catalysts.

Preferred acid removal substances have low solubility in water and give phosphorus acid salts which also have very low solubility in water. The permissible metals which make up the acid removal substances include Group 2, 11 and 12 metals selected from calcium (Ca), silver (Ag), zinc (Zn) and the like. Illustrative metal oxides useful in this invention include, for example, calcium oxide, silver oxide, zinc oxide and the like. Illustrative hydroxides useful in this invention include, for example, calcium hydroxide, zinc hydroxide and the like. Illustrative carbonates useful in this invention include, for example, calcium carbonate, silver carbonate, zinc carbonate and the like. Illustrative carboxylates useful in this invention include, for example, calcium 2-ethylhexanoate.

Illustrative of suitable acid removal substances include those permissible acid removal substances described in Kirk-Othmer, Encyclopedia of Chemical Technology, Fourth Edition, 1996, the pertinent portions of which are incorporated herein by reference.

As indicated above, the reaction product fluid may contain at least some amount of various phosphorus acidic compounds, for example, $H_3PO_3$, aldehyde acids such as hydroxy alkyl phosphonic acids, $H_3PO$, and the like, and other acidic compounds, for example, carboxylic acids such as butyric acid, and the like. If the one or more acid removal substances should become saturated with carboxylic acids, the process of this invention can still be operated at desirably low levels of phosphorus acidic compounds. The stronger phosphorus acidic compounds are able to displace the weaker carboxylic acids from the acid removal substances in the operation of this invention.

In the embodiment of this invention involving treating at least a portion of the reaction product fluid derived from said process and which also contains phosphorus acidic compounds formed during said process by introducing one or more acid removal substances into the at least one reaction zone, the at least one separation zone, the at least one scrubber zone and/or the at least one acid removal zone sufficient to remove at least some amount of the phosphorus acidic compounds from said reaction product fluid or said contacted water, any precipitation of salts in the various zones may be removed by filtration or deposited on a support and removed by mechanical means. Also, for carboxylates, carboxylic acid may be added to the various zones and converted in situ to carboxylates or the carboxylate itself may be added directly to the various zones.

The removal of phosphorus acidic compounds from the reaction product fluid or water in accordance with this invention can be accomplished simply by contacting the reaction product fluid or water with the one or more acid removal substances. The quantity of acid removal substances relative to reaction product fluid or water will depend upon the quantity of phosphorus acidic compounds in the reaction product fluid or water. The quantity of acid removal substances need only be sufficient to reduce the phosphorus acidic compound concentration to the desired value. Based on a reaction product fluid or water standard having a phosphorus acidic compound concentration of about 10 parts per million, an amount, by volume, of acid removal substances of about 10 milliliters of acid removal substances per liter of reaction product fluid or water to be treated should be satisfactory for phosphorus acidic compound removal from the reaction product fluid or water.

The contact time between the one or more acid removal substances and the reaction product fluid or water containing phosphorus acidic compounds removed from the reaction product fluid need only be sufficient to remove at least some of the phosphorus acidic compounds from the water. The reaction product fluid and water containing phosphorus acidic compounds can be contacted with the one or more acid removal substances in either a batch or continuous (or semi-continuous) mode. When operating in a batch mode, the contact preferably involves agitation of a mixture of the reaction product fluid or water containing phosphorus acidic compounds and the one or more acid removal substances for about 0.01 to about 10 hours, more typically about 0.1 to about 5 hours, followed by any known separation technique, e.g., settling, centrifugation, filtration or the like. Preferably, the invention is practiced in a continuous mode by flowing the reaction product fluid or water containing phosphorus acidic compounds through one or more contained beds of the acid removal substances, e.g., a fixed bed, a moving bed or a fluidized bed, at a liquid flow rate ranging from about 0.1 to about 100 bed volumes per hour, more typically from about 1 to about 20 bed volumes per hour. The invention can employ any conventional apparatus designed for acid removal service, special designs are not required. Obviously, adequate contacting between the one or more acid removal substances and the reaction product fluid or water containing phosphorus acidic compounds is important to obtain best results. As recognized by those skilled in this technology, the one or more acid removal substance beds are used to remove phosphorus acidic compounds from the reaction product fluid or water until the level (concentration) of phosphorus acidic compounds in the treated reaction product fluid or water exiting the one or more acid removal substance beds decreases to a desired value.

The number of acid removal substance beds which may be used in this invention is not narrowly critical. One or more acid removal substance beds, e.g., a series of such beds, may be employed and any such bed may be easily removed and/or replaced as required or desired.

Optionally, an organic nitrogen compound may be added to the reaction product fluid, e.g., hydroformylation reaction product fluid, to scavenge the acidic hydrolysis byproducts formed upon hydrolysis of the organophosphorus ligand, as taught, for example, in U.S. Pat. No. 4,567,306. Such organic nitrogen compounds may be used to react with and to neutralize the acidic compounds by forming conversion product salts therewith, thereby preventing the metal, e.g., rhodium, from complexing with the acidic hydrolysis byproducts and thus helping to protect the activity of the metal, e.g., rhodium, catalyst while it is present in the reaction zone under reaction, e.g., hydroformylation, conditions. The choice of the organic nitrogen compound for this function is, in part, dictated by the desirability of using a basic material that is soluble in the reaction medium and does not tend to catalyze the formation of aldols and other condensation products at a significant rate or to unduly react with the product, e.g., aldehyde.

Such organic nitrogen compounds may contain from 2 to 30 carbon atoms, and preferably from 2 to 24 carbon atoms. Primary amines should be excluded from use as said organic nitrogen compounds. Preferred organic nitrogen compounds should have a distribution coefficient that favors solubility in the organic phase. In general more preferred organic nitrogen compounds useful for scavenging the phosphorus acidic compounds present in the reaction product fluid of this invention include those having a pKa value within ±3 of the pH of the contacted water employed. Most preferably the pKa value of the organic nitrogen compound will be essentially about the same as the pH of the water employed. Of course it is to be understood that while it may be preferred to employ only one such organic nitrogen compound at a time in any given process, if desired, mixtures of two or more different organic nitrogen compounds may also be employed in any given processes.

Illustrative organic nitrogen compounds include e.g., trialkylamines, such as triethylamine, tri-n-propylamine, tri-n-butylamine, tri-iso-butylamine, tri-iso-propylamine, tri-n-hexylamine, tri-n-octylamine, dimethyl-iso-propylamine, dimethyl-hexadecylamine, methyl-di-n-octylamine, and the like, as well as substituted derivatives thereof containing one or more noninterfering substituents such as hydroxy groups, for example triethanolamine, N-methyl-diethanolamine, tris-(3-hydroxypropyl)-amine, and the like. Heterocyclic amines can also be used such as pyridine, picolines, lutidines, collidines, N-methylpiperidine, N-methylmorpholine, N-2'-hydroxyethylmorpholine, quinoline, iso-quinoline, quinoxaline, acridien, quinuclidine, as well as, diazoles, triazole, diazine and triazine compounds, and the like. Also suitable for possible use are aromatic tertiary amines, such as N,N-dimethylaniline, N,N-diethylaniline, N,N-dimethyl-p-toluidine, N-methyldiphenylamine, N,N-dimethylbenzylamine, N,N-dimethyl-1-naphthylamine, and the like. Compounds containing two or more amino groups, such as N,N,N',N'-tetramethylethylene diamine and triethylene diamine (i.e. 1,4-diazabicyclo-[2,2,2]-octane) can also be mentioned.

Preferred organic nitrogen compounds useful for scavenging the phosphorus acidic compounds present in the reaction product fluids of the this invention are heterocyclic compounds selected from the group consisting of diazoles, triazoles, diazines and triazines, such as those disclosed and employed in copending U.S. patent application Ser. No. 08/756,789, filed on Nov. 26, 1996, the disclosure of which is incorporated herein by reference. For example, benzimidazole and benztriazole are preferred candidates for such use.

Illustrative of suitable organic nitrogen compounds include those permissible organic nitrogen compounds described in Kirk-Othmer, Encyclopedia of Chemical Technology, Fourth Edition, 1996, the pertinent portions of which are incorporated herein by reference.

The amount of organic nitrogen compound that may be present in the reaction product fluid for scavenging the phosphorus acidic compounds present in the reaction product fluids of the this invention is typically sufficient to provide a concentration of at least about 0.0001 moles of free organic nitrogen compound per liter of reaction product fluid. In general the ratio of organic nitrogen compound to total organophosphorus ligand (whether bound with rhodium or present as free organophosphorus ligand) is at least about 0.1:1 and even more preferably at least about 0.5:1. The upper limit on the amount of organic nitrogen compound employed is governed mainly only by economical considerations. Organic nitrogen compound: organophosphorus compound molar ratios of at least about 1:1 up to about 5:1 should be sufficient for most purpose.

It is to be understood the organic nitrogen compound employed to scavenge said phosphorus acidic compounds need not be the same as the heterocyclic nitrogen compound employed to protect the metal catalyst under harsh conditions such as exist in the product, e.g., aldehyde, vaporizer-separator, as taught in copending U.S. patent application Ser. No. 08/756,789, referred to above. However, if said organic nitrogen compound and said heterocyclic nitrogen compound are desired to be the same and perform both said functions in a given process, care should be taken to see that there will be a sufficient amount of the heterocyclic nitrogen compound present in the reaction medium to also provide that amount of free heterocyclic nitrogen compound in the process, e.g., hydroformylation vaporizer-separator, that will allow both desired functions to be achieved.

Accordingly the water will not only remove free phosphoric acidic compounds from the metal-organophosphorus ligand complex catalyst containing reaction product fluids, the water also surprisingly removes the phosphorus acidic material of the conversion product salt formed by the use of the organic nitrogen compound scavenger when employed, i.e., the phosphorus acid of said conversion product salt remains behind in the water, while the treated reaction product fluid, along with the reactivated (free) organic nitrogen compound is returned to the reaction zone.

Another problem that has been observed when organopolyphosphorus ligand promoted metal catalysts are employed in processes, e.g., continuous liquid catalyst recycle hydroformylation processes, that involve harsh conditions such as recovery of the aldehyde via a vaporizer-separator, i.e., the slow loss in catalytic activity of the catalysts is believed due at least in part to the harsh conditions such as exist in a vaporizer employed in the separation and recovery of the aldehyde product from its reaction product fluid. For instance, it has been found that when an organopolyphosphorus ligand promoted rhodium catalyst is placed under harsh conditions such as high temperature and low carbon monoxide partial pressure, that the catalyst deactivates at an accelerated pace with time, due most likely to the formation of an inactive or less active rhodium species, which may also be susceptible to precipitation under prolonged exposure to such harsh conditions. Such evidence is also consistent with the view that the active catalyst which under hydroformylation conditions is believed to comprise a complex of rhodium, organopolyphosphorus ligand, carbon monoxide and hydrogen, loses at least some of its coordinated carbon monoxide ligand during exposure to such harsh conditions as encountered in vaporization, which provides a route for the formation of catalytically inactive or less active rhodium species. The means for preventing or minimizing such catalyst deactivation and/or precipitation involves carrying out the invention described and taught in copending U.S. patent application Ser. No. 08/756,789, referred to above, which comprises carrying out the hydroformylation process under conditions of low carbon monoxide partial pressure in the presence of a free heterocyclic nitrogen compound as disclosed therein.

By way of further explanation it is believed the free heterocyclic nitrogen compound serves as a replacement ligand for the lost carbon monoxide ligand thereby forming a neutral intermediate metal species comprising a complex of the metal, organopolyphosphorus ligand, the heterocyclic nitrogen compound and hydrogen during such harsh conditions, e.g., vaporization separation, thereby preventing or minimizing the formation of any such above mentioned catalytic inactive or less active metal species. It is further theorized that the maintenance of catalytic activity, or the minimization of its deactivation, throughout the course of such continuous liquid recycle hydroformylation is due to regeneration of the active catalyst from said neutral intermediate metal species in the reactor (i.e. hydroformylation reaction zone) of the particular hydroformylation process involved. It is believed that under the higher syn gas pressure hydroformylation conditions in the reactor, the active catalyst complex comprising metal, e.g., rhodium, organopolyphosphorus ligand, carbon monoxide and hydrogen is regenerated as a result of some of the carbon monoxide in the reactant syn gas replacing the heterocyclic nitrogen ligand of the recycled neutral intermediate rhodium species. That is to say, carbon monoxide having a stronger ligand affinity for rhodium, replaces the more weakly bonded heterocyclic nitrogen ligand of the recycled neutral intermediate rhodium species that was formed during vaporization separation as mentioned above, thereby reforming the active catalyst in the hydroformylation reactor.

Thus the possibility of metal catalyst deactivation due to such harsh conditions is said to be minimized or prevented by carrying out such distillation of the desired product from the metal-organopolyphosphorus ligand catalyst containing reaction product fluids in the added presence of a free heterocyclic nitrogen compound having a five or six membered heterocyclic ring consisting of 2 to 5 carbon atoms and from 2 to 3 nitrogen atoms, at least one of said nitrogen atoms containing a double bond. Such free heterocyclic nitrogen compounds may be selected from the class consisting of diazole, triazole, diazine, and triazine compounds, such as, e.g., benzimidazole or benzotriazole, and the like. The term "free" as it applies to said heterocyclic nitrogen compounds is employed therein to exclude any acid salts of such heterocyclic nitrogen compounds, i.e., salt compounds formed by the reaction of any phosphorus acidic compound present in the reaction product fluid with such free heterocyclic nitrogen compounds as discussed herein above.

It is to be understood that while it may be preferred to employ only one free heterocyclic nitrogen compound at a time in any given process, if desired, mixtures of two or more different free heterocyclic nitrogen compounds may also be employed in any given process. Moreover the amount of such free heterocyclic nitrogen compounds present during harsh conditions, e.g., the vaporization procedure, need only be that minimum amount necessary to furnish the basis for at least some minimization of such catalyst deactivation as might be found to occur as a result of carrying out an identical metal catalyzed liquid recycle hydroformylation process under essentially the same conditions, in the absence of any free heterocyclic nitrogen compound during vaporization separation of the aldehyde product. Amounts of such free heterocyclic nitrogen compounds ranging from about 0.01 up to about 10 weight percent, or higher if desired, based on the total weight of the reaction product fluid to be distilled should be sufficient for most purposes.

An alternate method of transferring acidity from the reaction product fluid to an aqueous fraction is through the intermediate use of a heterocyclic amine which has a fluorocarbon or silicone side chain of sufficient size that it is immiscible in both the reaction product fluid and in the aqueous fraction. The heterocyclic amine may first be contacted with the reaction product fluid where the acidity present in the reaction product fluid will be transferred to the nitrogen of the heterocyclic amine. This heterocyclic amine layer may then be decanted or otherwise separated from the reaction product fluid before contacting it with the aqueous fraction where it again would exist as a separate phase. The heterocyclic amine layer may then be returned to contact the reaction product fluid.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds which can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

We claim:

1. A process for separating one or more phosphorus acidic compounds from a reaction product fluid containing said one or more phosphorus acidic compounds, a metal-organophosphorus ligand complex catalyst and optionally free organophosphorus ligand which process comprises (a) treating said reaction product fluid with water sufficient to remove at least some amount of said one or more phosphorus acidic compounds from said reaction product fluid and (b) treating the water which contains phosphorus acidic compounds removed from said reaction product fluid with an acid removal substance sufficient to remove at least some amount of said one or more phosphorus acidic compounds from said water, wherein said metal-organophosphorus ligand complex catalyst comprises a Group 8, 9 or 10 metal complexed with an organophosphorus ligand selected from the following:

(i) a monoorganophosphorus ligand represented by the formula:

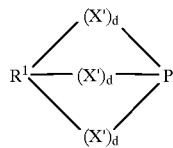

wherein $R^1$ represents a substituted or unsubstituted trivalent hydrocarbon radical containing from 4 to 40 carbon atoms or greater, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, and each d is the same or different and is a value of 0 or 1, provided that the normal valencies of $R^1$, X' and phosphorus (P) are satisfied;

(ii) a diorganophosphorus ligand represented by the formula:

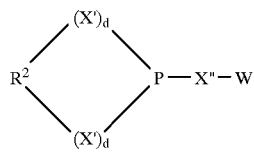

wherein $R^2$ represents a substituted or unsubstituted divalent hydrocarbon radical containing from 4 to 40 carbon atoms or greater, W represents a substituted or unsubstituted monovalent hydrocarbon radical containing from 1 to 18 carbon atoms or greater, X" represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' and X" is other than a substituted or unsubstituted divalent hydrocarbon radical containing from 2 to 40 carbon atoms or greater and at least one X' and X" is other than an oxygen (O) atom, and each d is the same or different and is a value of 0 or 1, provided that the normal valencies of $R^2$, X' and phosphorus (P) are satisfied;

(iii) a triorganophosphorus ligand represented by the formula:

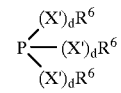

wherein each $R^6$ is the same or different and represents a substituted or unsubstituted monovalent hydrocarbon radical, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, and each d is the same or different and is a value of 0 or 1, provided that the normal valencies of $R^6$, X' and phosphorus (P) are satisfied; and (iv) an organopolyphosphorus ligand containing two or more tertiary (trivalent) phosphorus atoms represented by the formula:

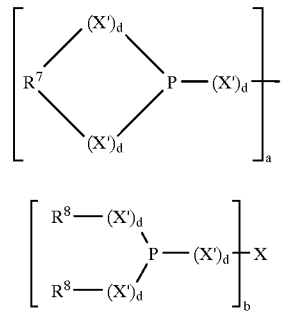

wherein X represents a substituted or unsubstituted n-valent hydrocarbon bridging radical containing from 2 to 40 carbon atoms, each $R^7$ is the same or different and represents a divalent hydrocarbon radical containing from 4 to 40 carbon atoms, each $R^8$ is the same or different and represents a substituted or unsubstituted monovalent hydrocarbon radical containing from 1 to 24 carbon atoms, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, a and b can be the same or different and each have a value of 0 to 6, with the proviso that the sum of a+b is 2 to 6 and n equals a+b, and each d is the same or different and is a value of 0 or 1, provided that the normal valencies of $R^7$, $R^8$, X', X and phosphorus (P) are satisfied.

2. A process for stabilizing an organophosphorus ligand against hydrolytic degradation and/or a metal-organophosphorus ligand complex catalyst against deactivation which process comprises (a) treating a reaction product fluid containing a metal-organophosphorus ligand complex catalyst and optionally free organophosphorus ligand and which also contains one or more phosphorus acidic compounds, with water sufficient to remove at least some amount of said one or more phosphorus acidic compounds from said reaction product fluid and (b) treating the water which contains phosphorus acidic compounds removed from said reaction product fluid with an acid removal substance sufficient to remove at least some amount of said one or more phosphorus acidic compounds from said water, wherein said organophosphorus ligand is selected from the following and said metal-organophosphorus ligand complex catalyst comprises a Group 8, 9 or 10 metal complexed with an organophosphorus ligand selected from the following:

(i) a monoorganophosphorus ligand represented by the formula:

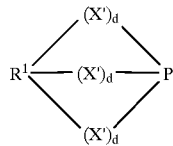

wherein $R^1$ represents a substituted or unsubstituted trivalent hydrocarbon radical containing from 4 to 40 carbon atoms or greater, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, and each d is the same or different and is a value of 0 or 1, provided that the normal valencies of $R^1$, X' and phosphorus (P) are satisfied;

(ii) a diorganophosphorus ligand represented by the formula:

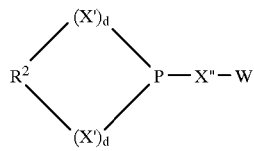

wherein $R^2$ represents a substituted or unsubstituted divalent hydrocarbon radical containing from 4 to 40 carbon atoms or greater, W represents a substituted or unsubstituted monovalent hydrocarbon radical containing from 1 to 18 carbon atoms or greater, X" represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' and X" is other than a substituted or unsubstituted divalent hydrocarbon radical containing from 2 to 40 carbon atoms or greater and at least one X' and X" is other than an oxygen (O) atom, and each d is the same or different and is a value of 0 or 1, provided that the normal valencies of $R^2$, X' and phosphorus (P) are satisfied;

(iii) a triorganophosphorus ligand represented by the formula:

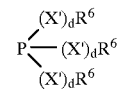

wherein each $R^6$ is the same or different and represents a substituted or unsubstituted monovalent hydrocarbon radical, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, and each d is the same or different and is a value of 0 or 1, provided that the normal valencies of $R^6$, X' and phosphorus (P) are satisfied; and (iv) an organopolyphosphorus ligand containing two or more tertiary (trivalent) phosphorus atoms represented by the formula:

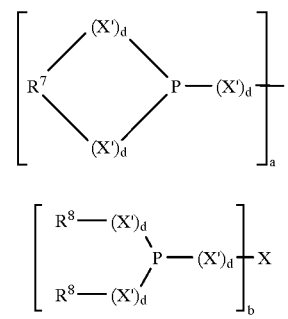

wherein X represents a substituted or unsubstituted n-valent hydrocarbon bridging radical containing from 2 to 40 carbon atoms, each $R^7$ is the same or different and represents a divalent hydrocarbon radical containing from 4 to 40 carbon atoms, each $R^8$ is the same or different and represents a substituted or unsubstituted monovalent hydrocarbon radical containing from 1 to 24 carbon atoms, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, a and b can be the same or different and each have a value of 0 to 6, with the proviso that the sum of a+b is 2 to 6 and n equals a+b, and each d is the same or different and is a value of 0 or 1, provided that the normal valencies of $R^7$, $R^8$, X', X and phosphorus (P) are satisfied.

3. A process for preventing and/or lessening hydrolytic degradation of an organophosphorus ligand and/or deactivation of a metal-organophosphorus ligand complex catalyst which process comprises (a) treating a reaction product fluid containing a metal-organophosphorus ligand complex catalyst and optionally free organophosphorus ligand and which also contains one or more phosphorus acidic compounds, with water sufficient to remove at least some amount of said one or more phosphorus acidic compounds from said reaction product fluid and (b) treating the water which contains phosphorus acidic compounds removed from said reaction product fluid with an acid removal substance sufficient to remove at least some amount of said one or more phosphorus acidic compounds from said water, wherein said organophosphorus ligand is selected from the following and said metal-organophosphorus ligand complex catalyst comprises a Group 8, 9 or 10 metal complexed with an organophosphorus ligand selected from the following:

(i) a monoorganophosphorus ligand represented by the formula:

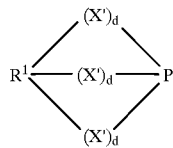

wherein $R^1$ represents a substituted or unsubstituted trivalent hydrocarbon radical containing from 4 to 40 carbon atoms or greater, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, and each d is the same or different and is a value of 0 or 1, provided that the normal valencies of $R^1$, X' and phosphorus (P) are satisfied;

(ii) a diorganophosphorus ligand represented by the formula:

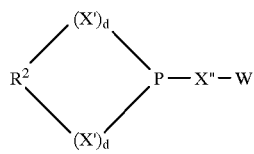

wherein $R^2$ represents a substituted or unsubstituted divalent hydrocarbon radical containing from 4 to 40 carbon atoms or greater, W represents a substituted or unsubstituted monovalent hydrocarbon radical containing from 1 to 18 carbon atoms or greater, X" represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' and X" is other than a substituted or unsubstituted divalent hydrocarbon radical containing from 2 to 40 carbon atoms or greater and at least one X' and X" is other than an oxygen (O) atom, and each d is the same or different and is a value of 0 or 1, provided that the normal valencies of $R^2$, X' and phosphorus (P) are satisfied;

(iii) a triorganophosphorus ligand represented by the formula:

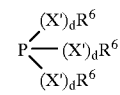

wherein each $R^6$ is the same or different and represents a substituted or unsubstituted monovalent hydrocarbon radical, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, and each d is the same or different and is a value of 0 or 1, provided that the normal valencies of $R^6$, X' and phosphorus (P) are satisfied; and (iv) an organopolyphosphorus ligand containing two or more tertiary (trivalent) phosphorus atoms represented by the formula:

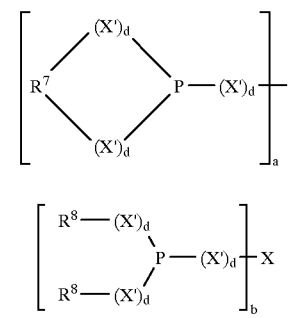

wherein X represents a substituted or unsubstituted n-valent hydrocarbon bridging radical containing from 2 to 40 carbon atoms, each $R^7$ is the same or different and represents a divalent hydrocarbon radical containing from 4 to 40 carbon atoms, each $R^8$ is the same or different and represents a substituted or unsubstituted monovalent hydrocarbon radical containing from 1 to 24 carbon atoms, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, a and b can be the same or different and each have a value of 0 to 6, with the proviso that the sum of a+b is 2 to 6 and n equals a+b, and each d is the same or different and is a value of 0 or 1, provided that the normal valencies of $R^7$, $R^8$, X', X and phosphorus (P) are satisfied.

4. An improved process which comprises reacting one or more reactants in the presence of a metal-organophosphorus ligand complex catalyst and optionally free organophosphorus ligand to produce a reaction product fluid comprising one or more products, the improvement comprising preventing and/or lessening hydrolytic degradation of the organophosphorus ligand and deactivation of the metal-organophosphorus ligand complex catalyst by treating at least a portion of said reaction product fluid derived from said process and which also contains phosphorus acidic compounds formed during said process with one or more acid removal substances sufficient to remove at least some amount of the phosphorus acidic compounds from said reaction product fluid, wherein said organophosphorus ligand is selected from the following and said metal-organophosphorus ligand complex catalyst comprises a Group 8, 9 or 10 metal complexed with an organophosphorus ligand selected from the following:

(i) a monoorganophosphorus ligand represented by the formula:

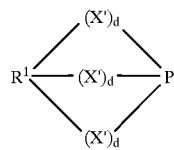

wherein $R^1$ represents a substituted or unsubstituted trivalent hydrocarbon radical containing from 4 to 40 carbon atoms or greater, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, and each d is the same or different and is a value of 0 or 1, provided that the normal valencies of $R^1$, X' and phosphorus (P) are satisfied;

(ii) a diorganophosphorus ligand represented by the formula:

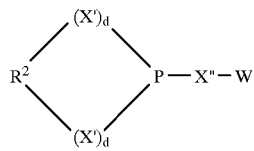

wherein $R^2$ represents a substituted or unsubstituted divalent hydrocarbon radical containing from 4 to 40 carbon atoms or greater, W represents a substituted or unsubstituted monovalent hydrocarbon radical containing from 1 to 18 carbon atoms or greater, X" represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' and X" is other than a substituted or unsubstituted divalent hydrocarbon radical containing from 2 to 40 carbon atoms or greater and at least one X' and X" is other than an oxygen (O) atom, and each d is the same or different and is a value of 0 or 1, provided that the normal valencies of $R^2$, X' and phosphorus (P) are satisfied;

(iii) a triorganophosphorus ligand represented by the formula:

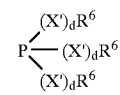

wherein each $R^6$ is the same or different and represents a substituted or unsubstituted monovalent hydrocarbon radical, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, and each d is the same or different and is a value of 0 or 1, provided that the normal valencies of $R^6$, X' and phosphorus (P) are satisfied; and (iv) an organopolyphosphorus ligand containing two or more tertiary (trivalent) phosphorus atoms represented by the formula:

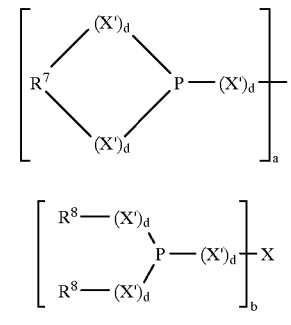

wherein X represents a substituted or unsubstituted n-valent hydrocarbon bridging radical containing from 2 to 40 carbon atoms, each $R^7$ is the same or different and represents a divalent hydrocarbon radical containing from 4 to 40 carbon atoms, each $R^8$ is the same or different and represents a substituted or unsubstituted monovalent hydrocarbon radical containing from 1 to 24 carbon atoms, each X' is the same or different and represents an oxygen (O) atom, a substituted or unsubstituted divalent nitrogen (N) atom-containing radical, a substituted or unsubstituted divalent sulfur (S)

atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, a and b can be the same or different and each have a value of 0 to 6, with the proviso that the sum of a+b is 2 to 6 and n equals a+b, and each d is the same or different and is a value of 0 or 1, provided that the normal valencies of $R^7$, $R^8$, X', X and phosphorus (P) are satisfied.

5. The improved process of claim 4 which comprises (i) reacting in at least one reaction zone one or more reactants in the presence of a metal-organophosphorus ligand complex catalyst and optionally free organophosphorus ligand to produce a reaction product fluid comprising one or more products and (ii) separating in at least one separation zone or in said at least one reaction zone the one or more products from said reaction product fluid, the improvement comprising preventing and/or lessening hydrolytic degradation of any said organophosphorus ligand and deactivation of said metal-organophosphorus ligand complex catalyst by (a) treating in at least one scrubber zone at least a portion of said reaction product fluid derived from said process and which also contains phosphorus acidic compounds formed during said process with water sufficient to remove at least some amount of the phosphorus acidic compounds from said reaction product fluid and (b) treating in at least one acid removal zone at least a portion of the water which contains phosphorus acidic compounds removed from said reaction product fluid with one or more acid removal substances sufficient to remove at least some amount of the phosphorus acidic compounds from said water, wherein said organophosphorus ligand is selected from the following and said metal-organophosphorus ligand complex catalyst comprises a Group 8, 9 or 10 metal complexed with an organophosphorus ligand selected from the following:

(i) a monoorganophosphorus ligand represented by the formula:

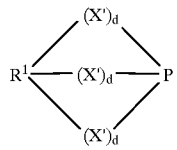

wherein $R^1$ represents a substituted or unsubstituted trivalent hydrocarbon radical containing from 4 to 40 carbon atoms or greater, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, and each d is the same or different and is a value of 0 or 1, provided that the normal valencies of $R^1$, X' and phosphorus (P) are satisfied;

(ii) a diorganophosphorus ligand represented by the formula:

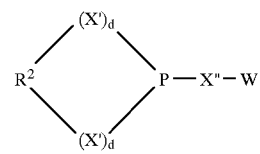

wherein $R^2$ represents a substituted or unsubstituted divalent hydrocarbon radical containing from 4 to 40 carbon atoms or greater, W represents a substituted or unsubstituted monovalent hydrocarbon radical containing from 1 to 18 carbon atoms or greater, X" represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' and X" is other than a substituted or unsubstituted divalent hydrocarbon radical containing from 2 to 40 carbon atoms or greater and at least one X' and X" is other than an oxygen (O) atom, and each d is the same or different and is a value of 0 or 1, provided that the normal valencies of $R^2$, X' and phosphorus (P) are satisfied;

(iii) a triorganophosphorus ligand represented by the formula:

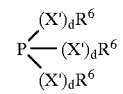

wherein each $R^6$ is the same or different and represents a substituted or unsubstituted monovalent hydrocarbon radical, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, and each d is the same or different and is a value of 0 or 1, provided that the normal valencies of $R^6$, X' and phosphorus (P) are satisfied; and (iv) an organopolyphosphorus ligand containing two or more tertiary (trivalent) phosphorus atoms represented by the formula:

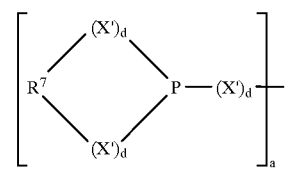

-continued

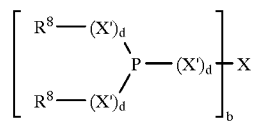

wherein X represents a substituted or unsubstituted n-valent hydrocarbon bridging radical containing from 2 to 40 carbon atoms, each $R^7$ is the same or different and represents a divalent hydrocarbon radical containing from 4 to 40 carbon atoms, each $R^8$ is the same or different and represents a substituted or unsubstituted monovalent hydrocarbon radical containing from 1 to 24 carbon atoms, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, a and b can be the same or different and each have a value of 0 to 6, with the proviso that the sum of a+b is 2 to 6 and n equals a+b, and each d is the same or different and is a value of 0 or 1, provided that the normal valencies of $R^7$, $R^8$, X', X and phosphorus (P) are satisfied.

6. The improved process of claim 4 which comprises (i) reacting in at least one reaction zone one or more reactants in the presence of a metal-organophosphorus ligand complex catalyst and optionally free organophosphorus ligand to produce a reaction product fluid comprising one or more products and (ii) separating in at least one separation zone or in said at least one reaction zone the one or more products from said reaction product fluid, the improvement comprising preventing and/or lessening hydrolytic degradation of any said organophosphorus ligand and deactivation of said metal-organophosphorus ligand complex catalyst by (a) treating in at least one acid removal zone at least a portion of said reaction product fluid derived from said process and which also contains phosphorus acidic compounds formed during said process with one or more acid removal substances sufficient to remove at least some amount of the phosphorus acidic compounds from said reaction product fluid, and (b) returning the treated reaction product fluid to said at least one reaction zone or said at least one separation zone, wherein said organophosphorus ligand is selected from the following and said metal-organophosphorus ligand complex catalyst comprises a Group 8, 9 or 10 metal complexed with an organophosphorus ligand selected from the following:

(i) a monoorganophosphorus ligand represented by the formula:

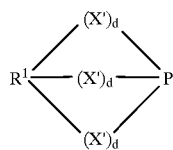

wherein $R^1$ represents a substituted or unsubstituted trivalent hydrocarbon radical containing from 4 to 40 carbon atoms or greater, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, and each d is the same or different and is a value of 0 or 1, provided that the normal valencies of $R^1$, X' and phosphorus (P) are satisfied;

(ii) a diorganophosphorus ligand represented by the formula:

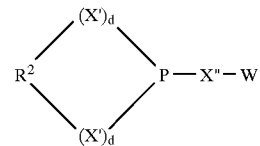

wherein $R^2$ represents a substituted or unsubstituted divalent hydrocarbon radical containing from 4 to 40 carbon atoms or greater, W represents a substituted or unsubstituted monovalent hydrocarbon radical containing from 1 to 18 carbon atoms or greater, X" represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' and X" is other than a substituted or unsubstituted divalent hydrocarbon radical containing from 2 to 40 carbon atoms or greater and at least one X' and X" is other than an oxygen (O) atom, and each d is the same or different and is a value of 0 or 1, provided that the normal valencies of $R^2$, X' and phosphorus (P) are satisfied;

(iii) a triorganophosphorus ligand represented by the formula:

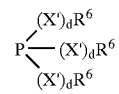

wherein each $R^6$ is the same or different and represents a substituted or unsubstituted monovalent hydrocarbon radical, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, and each d is the same or different and is a value of 0 or 1, provided that the normal valencies of $R^6$, X' and phosphorus (P) are satisfied; and (iv) an organopolyphosphorus ligand containing two or more tertiary (trivalent) phosphorus atoms represented by the formula:

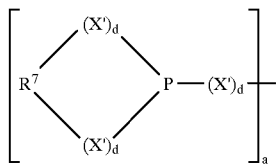

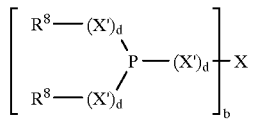

wherein X represents a substituted or unsubstituted n-valent hydrocarbon bridging radical containing from 2 to 40 carbon atoms, each $R^7$ is the same or different and represents a divalent hydrocarbon radical containing from 4 to 40 carbon atoms, each $R^8$ is the same or different and represents a substituted or unsubstituted monovalent hydrocarbon radical containing from 1 to 24 carbon atoms, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, a and b can be the same or different and each have a value of 0 to 6, with the proviso that the sum of a+b is 2 to 6 and n equals a+b, and each d is the same or different and is a value of 0 or 1, provided that the normal valencies of $R^7$, $R^8$, X', X and phosphorus (P) are satisfied.

7. The improved process of claim 4 which comprises (i) reacting in at least one reaction zone one or more reactants in the presence of a metal-organophosphorus ligand complex catalyst and optionally free organophosphorus ligand to produce a reaction product fluid comprising one or more products and (ii) separating in at least one separation zone or in said at least one reaction zone the one or more products from said reaction product fluid, the improvement comprising preventing and/or lessening hydrolytic degradation of any said organophosphorus ligand and deactivation of said metal-organophosphorus ligand complex catalyst by (a) treating in at least one scrubber zone at least a portion of said reaction product fluid derived from said process and which also contains phosphorus acidic compounds formed during said process with water sufficient to remove at least some amount of the phosphorus acidic compounds from said reaction product fluid, (b) returning the treated reaction product fluid to said at least one reaction zone or said at least one separation zone, (c) treating in at least one acid removal zone at least a portion of the water which contains phosphorus acidic compounds removed from said reaction product fluid with one or more acid removal substances sufficient to remove at least some amount of the phosphorus acidic compounds from said water, and (d) returning the treated water to said at least one scrubber zone, wherein said organophosphorus ligand is selected from the following and said metal-organophosphorus ligand complex catalyst comprises a Group 8, 9 or 10 metal complexed with an organophosphorus ligand selected from the following:

(i) a monoorganophosphorus ligand represented by the formula:

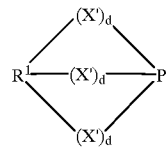

wherein $R^1$ represents a substituted or unsubstituted trivalent hydrocarbon radical containing from 4 to 40 carbon atoms or greater, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, and each d is the same or different and is a value of 0 or 1, provided that the normal valencies of $R^1$, X' and phosphorus (P) are satisfied;

(ii) a diorganophosphorus ligand represented by the formula:

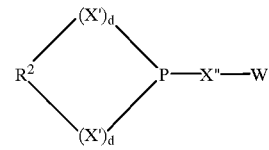

wherein $R^2$ represents a substituted or unsubstituted divalent hydrocarbon radical containing from 4 to 40 carbon atoms or greater, W represents a substituted or unsubstituted monovalent hydrocarbon radical containing from 1 to 18 carbon atoms or greater, X" represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' and X" is other than a substituted or unsubstituted divalent hydrocarbon radical containing from 2 to 40 carbon atoms or greater and at least one X' and X" is other than an oxygen (O) atom, and each d is the same or different and is a value of 0 or 1, provided that the normal valencies of $R^2$, X' and phosphorus (P) are satisfied;

(iii) a triorganophosphorus ligand represented by the formula:

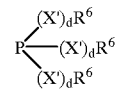

wherein each $R^6$ is the same or different and represents a substituted or unsubstituted monovalent hydrocarbon radical, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, and each d is the same or different and is a value of 0 or 1, provided that the normal valencies of $R^6$, X' and phosphorus (P) are satisfied; and (iv) an organopolyphosphorus ligand containing two or more tertiary (trivalent) phosphorus atoms represented by the formula:

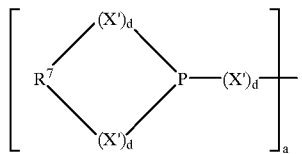

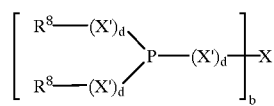

wherein X represents a substituted or unsubstituted n-valent hydrocarbon bridging radical containing from 2 to 40 carbon atoms, each $R^7$ is the same or different and represents a divalent hydrocarbon radical containing from 4 to 40 carbon atoms, each $R^8$ is the same or different and represents a substituted or unsubstituted monovalent hydrocarbon radical containing from 1 to 24 carbon atoms, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, a and b can be the same or different and each have a value of 0 to 6, with the proviso that the sum of a+b is 2 to 6 and n equals a+b, and each d is the same or different and is a value of 0 or 1, provided that the normal valencies of $R^7$, $R^8$, X', X and phosphorus (P) are satisfied.

8. The improved process of claim 4 which comprises (i) reacting in at least one reaction zone one or more reactants in the presence of a metal-organophosphorus ligand complex catalyst and optionally free organophosphorus ligand to produce a reaction product fluid comprising one or more products and (ii) separating in at least one separation zone or in said at least one reaction zone the one or more products from said reaction product fluid, the improvement comprising preventing and/or lessening hydrolytic degradation of any said organophosphorus ligand and deactivation of said metal-organophosphorus ligand complex catalyst by (a) withdrawing from said at least one reaction zone or said at least one separation zone at least a portion of a reaction product fluid derived from said process and which also contains phosphorus acidic compounds formed during said process, (b) treating in at least one acid removal zone at least a portion of the withdrawn reaction product fluid derived from said process and which also contains phosphorus acidic compounds formed during said process with one or more acid removal substances sufficient to remove at least some amount of the phosphorus acidic compounds from said reaction product fluid, (c) returning the treated reaction product fluid to said at least one reaction zone or said at least one separation zone, and (d) optionally replacing said one or more acid removal substances, wherein said organophosphorus ligand is selected from the following and said metal-organophosphorus ligand complex catalyst comprises a Group 8, 9 or 10 metal complexed with an organophosphorus ligand selected from the following:

(i) a monoorganophosphorus ligand represented by the formula:

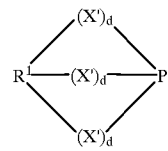

wherein $R^1$ represents a substituted or unsubstituted trivalent hydrocarbon radical containing from 4 to 40 carbon atoms or greater, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, and each d is the same or different and is a value of 0 or 1, provided that the normal valencies of $R^1$, X' and phosphorus (P) are satisfied;

(ii) a diorganophosphorus ligand represented by the formula:

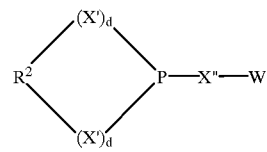

wherein $R^2$ represents a substituted or unsubstituted divalent hydrocarbon radical containing from 4 to 40 carbon atoms or greater, W represents a substituted or unsubstituted monovalent hydrocarbon radical containing from 1 to 18 carbon atoms or greater, X" represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' and X" is other than a substituted or unsubstituted divalent hydrocarbon radical containing from 2 to 40 carbon atoms or greater and at least one X' and X" is other than an oxygen (O) atom, and each d is the same or different and is a value of 0 or 1, provided that the normal valencies of $R^2$, X' and phosphorus (P) are satisfied;

(iii) a triorganophosphorus ligand represented by the formula:

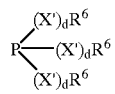

wherein each R⁶ is the same or different and represents a substituted or unsubstituted monovalent hydrocarbon radical, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, and each d is the same or different and is a value of 0 or 1, provided that the normal valencies of R⁶, X' and phosphorus (P) are satisfied; and (iv) an organopolyphosphorus ligand containing two or more tertiary (trivalent) phosphorus atoms represented by the formula:

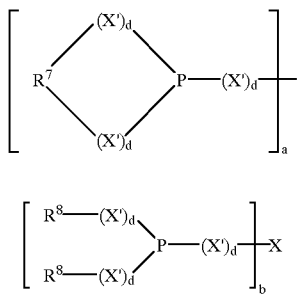

wherein X represents a substituted or unsubstituted n-valent hydrocarbon bridging radical containing from 2 to 40 carbon atoms, each R⁷ is the same or different and represents a divalent hydrocarbon radical containing from 4 to 40 carbon atoms, each R⁸ is the same or different and represents a substituted or unsubstituted monovalent hydrocarbon radical containing from 1 to 24 carbon atoms, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, a and b can be the same or different and each have a value of 0 to 6, with the proviso that the sum of a+b is 2 to 6 and n equals a+b, and each d is the same or different and is a value of 0 or 1, provided that the normal valencies of R⁷, R⁸, X', X and phosphorus (P) are satisfied.

9. The improved process of claim 4 which comprises (i) reacting in at least one reaction zone one or more reactants in the presence of a metal-organophosphorus ligand complex catalyst and optionally free organophosphorus ligand to produce a reaction product fluid comprising one or more products and (ii) separating in at least one separation zone or in said at least one reaction zone the one or more products from said reaction product fluid, the improvement comprising preventing and/or lessening hydrolytic degradation of any said organophosphorus ligand and deactivation of said metal-organophosphorus ligand complex catalyst by (a) withdrawing from said at least one reaction zone or said at least one separation zone at least a portion of a reaction product fluid derived from said process and which also contains phosphorus acidic compounds formed during said process, (b) treating in at least one scrubber zone at least a portion of the withdrawn reaction product fluid derived from said process and which also contains phosphorus acidic compounds formed during said process with water sufficient to remove at least some amount of the phosphorus acidic compounds from said reaction product fluid, (c) returning the treated reaction product fluid to said at least one reaction zone or said at least one separation zone, (d) withdrawing from said at least one scrubber zone at least a portion of said water which contains phosphorus acidic compounds removed from said reaction product fluid, (e) treating in at least one acid removal zone at least a portion of the withdrawn water which contains phosphorus acidic compounds removed from said reaction product fluid with one or more acid removal substances sufficient to remove at least some amount of the phosphorus acidic compounds from said water, (f) returning the treated water to said at least one scrubber zone, and (g) optionally replacing said one or more acid removal substances, wherein said organophosphorus ligand is selected from the following and said metal-organophosphorus ligand complex catalyst comprises a Group 8, 9 or 10 metal complexed with an organophosphorus ligand selected from the following:

(i) a monoorganophosphorus ligand represented by the formula:

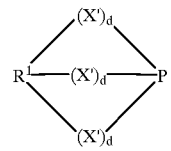

wherein R¹ represents a substituted or unsubstituted trivalent hydrocarbon radical containing from 4 to 40 carbon atoms or greater, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, and each d is the same or different and is a value of 0 or 1, provided that the normal valencies of R¹, X' and phosphorus (P) are satisfied;

(ii) a diorganophosphorus ligand represented by the formula:

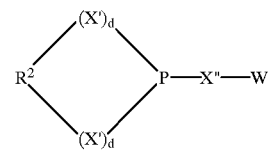

wherein R² represents a substituted or unsubstituted divalent hydrocarbon radical containing from 4 to 40 carbon atoms or greater, W represents a substituted or unsubstituted monovalent hydrocarbon radical containing from 1 to 18 carbon atoms or greater, X" represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' and X" is other than a substituted or unsubstituted divalent hydrocarbon radical containing from 2 to 40 carbon atoms or greater and at least one X' and X" is other than an oxygen (O) atom, and each d is the same or different and is a value of 0 or 1, provided that the normal valencies of $R^2$, X' and phosphorus (P) are satisfied;

(iii) a triorganophosphorus ligand represented by the formula:

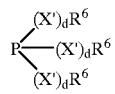

wherein each $R^6$ is the same or different and represents a substituted or unsubstituted monovalent hydrocarbon radical, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, and each d is the same or different and is a value of 0 or 1, provided that the normal valencies of $R^6$, X' and phosphorus (P) are satisfied; and (iv) an organopolyphosphorus ligand containing two or more tertiary (trivalent) phosphorus atoms represented by the formula:

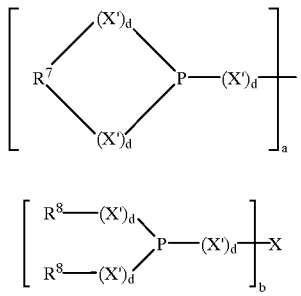

wherein X represents a substituted or unsubstituted n-valent hydrocarbon bridging radical containing from 2 to 40 carbon atoms, each $R^7$ is the same or different and represents a divalent hydrocarbon radical containing from 4 to 40 carbon atoms, each $R^8$ is the same or different and represents a substituted or unsubstituted monovalent hydrocarbon radical containing from 1 to 24 carbon atoms, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, a and b can be the same or different and each have a value of 0 to 6, with the proviso that the sum of a+b is 2 to 6 and n equals a+b, and each d is the same or different and is a value of 0 or 1, provided that the normal valencies of $R^7$, $R^8$, X', X and phosphorus (P) are satisfied.

10. The improved process of claim 4 which comprises (i) reacting in at least one reaction zone one or more reactants in the presence of a metal-organophosphorus ligand complex catalyst and optionally free organophosphorus ligand to produce a reaction product fluid comprising one or more products and (ii) separating in at least one separation zone or in said at least one reaction zone the one or more products from said reaction product fluid, the improvement comprising preventing and/or lessening hydrolytic degradation of any said organophosphorus ligand and deactivation of said metal-organophosphorus ligand complex catalyst by treating at least a portion of said reaction product fluid derived from said process and which also contains phosphorus acidic compounds formed during said process by introducing one or more acid removal substances into said at least one reaction zone and/or said at least one separation zone sufficient to remove at least some amount of the phosphorus acidic compounds from said reaction product fluid, wherein said organophosphorus ligand is selected from the following and said metal-organophosphorus ligand complex catalyst comprises a Group 8, 9 or 10 metal complexed with an organophosphorus ligand selected from the following:

(i) a monoorganophosphorus ligand represented by the formula:

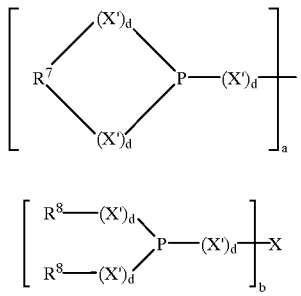

wherein $R^1$ represents a substituted or unsubstituted trivalent hydrocarbon radical containing from 4 to 40 carbon atoms or greater, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, and each d is the same or different and is a value of 0 or 1, provided that the normal valencies of $R^1$, X' and phosphorus (P) are satisfied;

(ii) a diorganophosphorus ligand represented by the formula:

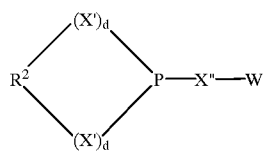

wherein R² represents a substituted or unsubstituted divalent hydrocarbon radical containing from 4 to 40 carbon atoms or greater, W represents a substituted or unsubstituted monovalent hydrocarbon radical containing from 1 to 18 carbon atoms or greater, X" represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' and X" is other than a substituted or unsubstituted divalent hydrocarbon radical containing from 2 to 40 carbon atoms or greater and at least one X' and X" is other than an oxygen (O) atom, and each d is the same or different and is a value of 0 or 1, provided that the normal valencies of R², X' and phosphorus (P) are satisfied;

(iii) a triorganophosphorus ligand represented by the formula:

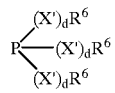

wherein each R⁶ is the same or different and represents a substituted or unsubstituted monovalent hydrocarbon radical, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, and each d is the same or different and is a value of 0 or 1, provided that the normal valencies of R⁶, X' and phosphorus (P) are satisfied; and (iv) an organopolyphosphorus ligand containing two or more tertiary (trivalent) phosphorus atoms represented by the formula:

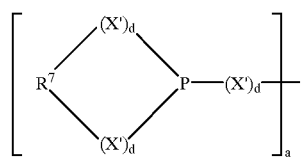

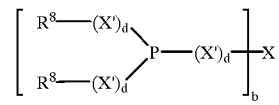

wherein X represents a substituted or unsubstituted n-valent hydrocarbon bridging radical containing from 2 to 40 carbon atoms, each R⁷ is the same or different and represents a divalent hydrocarbon radical containing from 4 to 40 carbon atoms, each R⁸ is the same or different and represents a substituted or unsubstituted monovalent hydrocarbon radical containing from 1 to 24 carbon atoms, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, a and b can be the same or different and each have a value of 0 to 6, with the proviso that the sum of a+b is 2 to 6 and n equals a+b, and each d is the same or different and is a value of 0 or 1, provided that the normal valencies of R⁷, R⁸, X', X and phosphorus (P) are satisfied.

11. The improved process of claim 4 which comprises (i) reacting in at least one reaction zone one or more reactants in the presence of a metal-organophosphorus ligand complex catalyst and optionally free organophosphorus ligand to produce a reaction product fluid comprising one or more products and (ii) separating in at least one separation zone or in said at least one reaction zone the one or more products from said reaction product fluid, the improvement comprising preventing and/or lessening hydrolytic degradation of any said organophosphorus ligand and deactivation of said metal-organophosphorus ligand complex catalyst by (a) treating at least a portion of said reaction product fluid derived from said process and which also contains phosphorus acidic compounds formed during said process by introducing water into said at least one reaction zone and/or said at least one separation zone sufficient to remove at least some amount of the phosphorus acidic compounds from said reaction product fluid and (b) treating in at least one acid removal zone at least a portion of the water which contains phosphorus acidic compounds removed from said reaction product fluid with one or more acid removal substances sufficient to remove at least some amount of the phosphorus acidic compounds from said water, wherein said organophosphorus ligand is selected from the following and said metal-organophosphorus ligand complex catalyst comprises a Group 8, 9 or 10 metal complexed with an organophosphorus ligand selected from the following:

(i) a monoorganophosphorus ligand represented by the formula:

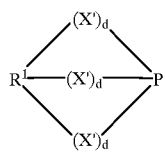

wherein $R^1$ represents a substituted or unsubstituted trivalent hydrocarbon radical containing from 4 to 40 carbon atoms or greater, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, and each d is the same or different and is a value of 0 or 1, provided that the normal valencies of $R^1$, X' and phosphorus (P) are satisfied;

(ii) a diorganophosphorus ligand represented by the formula:

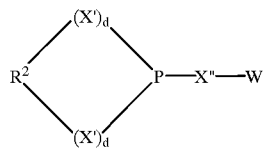

wherein $R^2$ represents a substituted or unsubstituted divalent hydrocarbon radical containing from 4 to 40 carbon atoms or greater, W represents a substituted or unsubstituted monovalent hydrocarbon radical containing from 1 to 18 carbon atoms or greater, X" represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' and X" is other than a substituted or unsubstituted divalent hydrocarbon radical containing from 2 to 40 carbon atoms or greater and at least one X' and X" is other than an oxygen (O) atom, and each d is the same or different and is a value of 0 or 1, provided that the normal valencies of $R^2$, X' and phosphorus (P) are satisfied;

(iii) a triorganophosphorus ligand represented by the formula:

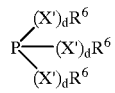

wherein each $R^6$ is the same or different and represents a substituted or unsubstituted monovalent hydrocarbon radical, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, and each d is the same or different and is a value of 0 or 1, provided that the normal valencies of $R^6$, X' and phosphorus (P) are satisfied; and (iv) an organopolyphosphorus ligand containing two or more tertiary (trivalent) phosphorus atoms represented by the formula:

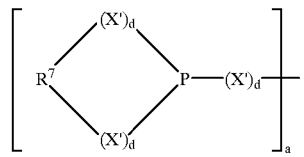

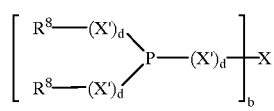

wherein X represents a substituted or unsubstituted n-valent hydrocarbon bridging radical containing from 2 to 40 carbon atoms, each $R^7$ is the same or different and represents a divalent hydrocarbon radical containing from 4 to 40 carbon atoms, each $R^8$ is the same or different and represents a substituted or unsubstituted monovalent hydrocarbon radical containing from 1 to 24 carbon atoms, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, a and b can be the same or different and each have a value of 0 to 6, with the proviso that the sum of a+b is 2 to 6 and n equals a+b, and each d is the same or different and is a value of 0 or 1, provided that the normal valencies of $R^7$, $R^8$, X', X and phosphorus (P) are satisfied.

12. The improved process of claim 4 which comprises (i) reacting in at least one reaction zone one or more reactants in the presence of a metal-organophosphorus ligand complex catalyst and optionally free organophosphorus ligand to produce a reaction product fluid comprising one or more products and (ii) separating in at least one separation zone or in said at least one reaction zone the one or more products from said reaction product fluid, the improvement comprising preventing and/or lessening hydrolytic degradation of any said organophosphorus ligand and deactivation of said metal-organophosphorus ligand complex catalyst by (a) withdrawing from said at least one reaction zone or said at least one separation zone at least a portion of a reaction product fluid derived from said process and which also contains phosphorus acidic compounds formed during said process, (b) treating in at least one scrubber zone at least a portion of the withdrawn reaction product fluid derived from said process and which also contains phosphorus acidic compounds formed during said process with water sufficient to remove at least some amount of the phosphorus acidic compounds from said reaction product fluid, (c) returning the treated reaction product fluid to said at least one reaction zone or said at least one separation zone, (d) treating in said at least one scrubber zone at least a portion of the water which contains phosphorus acidic compounds removed from said reaction product fluid with one or more acid removal substances sufficient to remove at least some amount of the phosphorus acidic compounds from said water, and (e) optionally replacing said one or more acid removal substances, wherein said organophosphorus ligand is selected from the following and said metal-organophosphorus ligand complex catalyst comprises a Group 8, 9 or 10 metal complexed with an organophosphorus ligand selected from the following:

(i) a monoorganophosphorus ligand represented by the formula:

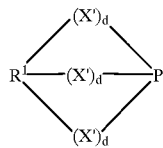

wherein $R^1$ represents a substituted or unsubstituted trivalent hydrocarbon radical containing from 4 to 40 carbon atoms or greater, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, and each d is the same or different and is a value of 0 or 1, provided that the normal valencies of $R^1$, X' and phosphorus (P) are satisfied;

(ii) a diorganophosphorus ligand represented by the formula:

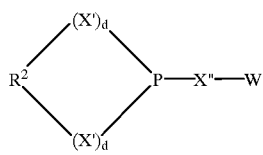

wherein $R^2$ represents a substituted or unsubstituted divalent hydrocarbon radical containing from 4 to 40 carbon atoms or greater, W represents a substituted or unsubstituted monovalent hydrocarbon radical containing from 1 to 18 carbon atoms or greater, X" represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' and X" is other than a substituted or unsubstituted divalent hydrocarbon radical containing from 2 to 40 carbon atoms or greater and at least one X' and X"
is other than an oxygen (O) atom, and each d is the same or different and is a value of 0 or 1, provided that the normal valencies of $R^2$, X' and phosphorus (P) are satisfied;

(iii) a triorganophosphorus ligand represented by the formula:

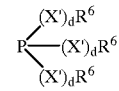

wherein each $R^6$ is the same or different and represents a substituted or unsubstituted monovalent hydrocarbon radical, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, and each d is the same or different and is a value of 0 or 1, provided that the normal valencies of $R^6$, X' and phosphorus (P) are satisfied; and (iv) an organopolyphosphorus ligand containing two or more tertiary (trivalent) phosphorus atoms represented by the formula:

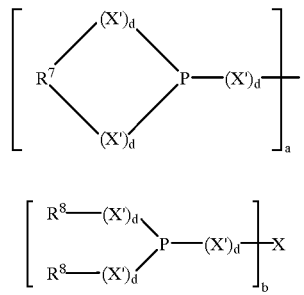

wherein X represents a substituted or unsubstituted n-valent hydrocarbon bridging radical containing from 2 to 40 carbon atoms, each $R^7$ is the same or different and represents a divalent hydrocarbon radical containing from 4 to 40 carbon atoms, each $R^8$ is the same or different and represents a substituted or unsubstituted monovalent hydrocarbon radical containing from 1 to 24 carbon atoms, each X' is the same or different and represents an oxygen (O) atom, a substituted or unsubstituted divalent nitrogen (N) atom-containing radical, a substituted or unsubstituted divalent sulfur (S) atom-containing radical or a substituted or unsubstituted divalent hydrocarbon radical containing from 2 to 40 carbon atoms or greater, provided at least one X' is other than a substituted or unsubstituted divalent hydrocarbon radical containing from 2 to 40 carbon atoms or greater and at least one X' is other than an oxygen (O) atom, a and b can be the same or different and each have a value of 0 to 6, with the proviso that the sum of a+b is 2 to 6 and n equals a+b and each d is the same or different and is a value of 0 or 1, provided that the normal valencies of $R^7$, $R^8$, X', X and phosphorus (P) are satisfied.

13. The process of claim 1 which comprises a hydroformylation, hydroacylation (intramolecular and intermolecular), hydrocyanation, hydroamidation, hydroesterification, aminolysis, alcoholysis, carbonylation, isomerization or transfer hydrogenation process.

14. The process of claim 1 wherein said acid removal substances are selected from oxides, hydroxides, carbonates, bicarbonates and carboxylates of Group 2, 11 and 12 metals.

15. The process of claim 1 wherein said reaction product fluid contains a homogeneous or heterogeneous metal-organophosphorus ligand complex catalyst or at least a portion of said reaction product fluid contacts a fixed heterogeneous metal-organophosphorus ligand complex catalyst during said processes.

16. The process of claim 5 wherein said separating of one or more products from the reaction product fluid occurs prior to or after treating at least a portion of the reaction product fluid derived from said processes and which also contains phosphorus acidic compounds formed during said processes with water.

17. The process of claim 1 wherein said metal-organophosphorus ligand complex catalyst comprises rhodium complexed with an organophosphorus ligand.

18. The process of claim 1 wherein phosphorus acidic compounds present in the reaction product fluid are scavenged by an organic nitrogen compound that is also present in said reaction medium and wherein at least some amount of the phosphorus acidic compound of the conversion products of the reaction between said phosphorus acidic compound and said organic nitrogen compound are also removed by the water treatment.

19. The process of claim 18 wherein the organic nitrogen compound is selected from the group consisting of diazoles, triazoles, diazines and triazines.

20. The process of claim 19 wherein the organic nitrogen compound is benzimidazole or benzotriazole.

* * * * *